United States Patent
Mohanty et al.

(10) Patent No.: US 10,857,238 B2
(45) Date of Patent: Dec. 8, 2020

(54) NANO-ENHANCED OPTICAL DELIVERY OF EXOGENOUS MOLECULES TO CELLS AND TISSUES

(71) Applicant: NANOSCOPE TECHNOLOGIES LLC, Arlington, TX (US)

(72) Inventors: Samarendra Kumar Mohanty, Bedford, TX (US); Sulagna Bhattacharya, Bedford, TX (US)

(73) Assignee: Nanoscope Technologies LLC, Bedford, TX (US)

( * ) Notice: Subject to any disclaimer, the term of this patent is extended or adjusted under 35 U.S.C. 154(b) by 0 days.

(21) Appl. No.: 16/074,041

(22) PCT Filed: Feb. 13, 2017

(86) PCT No.: PCT/US2017/017636
§ 371 (c)(1),
(2) Date: Jul. 30, 2018

(87) PCT Pub. No.: WO2017/139745
PCT Pub. Date: Aug. 17, 2017

(65) Prior Publication Data
US 2019/0038766 A1    Feb. 7, 2019

Related U.S. Application Data

(60) Provisional application No. 62/295,030, filed on Feb. 13, 2016.

(51) Int. Cl.
| | |
|---|---|
| *A61K 47/69* | (2017.01) |
| *A61K 41/00* | (2020.01) |
| *A61B 3/10* | (2006.01) |
| *A61B 3/135* | (2006.01) |
| *C12N 13/00* | (2006.01) |
| *A61B 3/12* | (2006.01) |
| *B82Y 20/00* | (2011.01) |
| *B82Y 30/00* | (2011.01) |
| *B82Y 5/00* | (2011.01) |
| *A61B 3/00* | (2006.01) |

(52) U.S. Cl.
CPC .......... *A61K 47/6929* (2017.08); *A61B 3/102* (2013.01); *A61B 3/135* (2013.01); *A61K 41/00* (2013.01); *A61K 47/6923* (2017.08); *C12N 13/00* (2013.01); *A61B 3/0008* (2013.01); *A61B 3/12* (2013.01); *B82Y 5/00* (2013.01); *B82Y 20/00* (2013.01); *B82Y 30/00* (2013.01)

(58) Field of Classification Search
None
See application file for complete search history.

(56) References Cited

U.S. PATENT DOCUMENTS

| | | |
|---|---|---|
| 6,803,994 B2 | 10/2004 | Margeson |
| 2011/0111002 A1 | 5/2011 | Pop |
| 2014/0012224 A1 | 1/2014 | Zhang et al. |
| 2015/0124219 A1 | 5/2015 | Horn et al. |

FOREIGN PATENT DOCUMENTS

| | | |
|---|---|---|
| CN | 203089533 U | 7/2013 |
| JP | 2009149593 A | 7/2009 |
| WO | 2014036194 A1 | 3/2014 |
| WO | 2014066598 A1 | 5/2014 |
| WO | 2014158263 A1 | 10/2014 |
| WO | 2015157761 A1 | 10/2015 |

OTHER PUBLICATIONS

Umanzor-Alvarez, Jose et al. "Near-infrared laser delivery of nanoparticles to developing embryos: a study of efficacy and viability." Biotechnology journal vol. 6,5 (2011): 519-24. doi:10.1002/biot.201000205 (Year: 2011).*
Adijanto, et al. (2015) "Nanoparticle-based technologies for retinal gene therapy." European Journal of Pharmaceutics and Biopharmaceutics, vol. 95:353-67. (Year: 2015).*
Wijaya, et al. (2008) "Selective Release of Multiple DNA Oligonucleotides from Gold Nanorods." ACS Nano, vol. 3(1):80-86. (Year: 2008).*
Baumgart, J., et. al.; "Plasmonic enhanced fs-laser optoporation of human melanoma cells," Frontiers in Ultrafast Optics: Biomedical, Scientific and Industrial Applications XI, SPIE; Proc. of SPIE vol. 7925 792501-1, pp. 1-6; Feb. 10, 2011.
Huang, Xiao, et. al.; "Light-activated RNA interference in human embryonic stem cells," 63 Biomaterials (2015) 70-79; Jun. 10, 2015.
Huschka, Ryan, et. al.; "Gene Silencing by Gold Nanoshell-Mediated Delivery and Laser-Triggered Release of Antisense Oligonucleotide and siRNA," ACS Nano, vol. 6, No. 9, Sep. 25, 2012, pp. 7681-7691.
Liao, Hongwei, et. al.; "Biomedical applicaitons of plasmon resonant metal nanoparticles," Nanomedicine (2005) 1(2), 201-208; Aug. 1, 2006.
Melancon, Marites P., et. al.; "Cancer Theranostics with Near-Infrared Light-Activatable Multimodal Nanoparticles," Accounts of Chemical Research, vol. 44, No. 10,pp. 947-956; Oct. 18, 2011.

(Continued)

*Primary Examiner* — Sean McGarry
(74) *Attorney, Agent, or Firm* — CrossPond Law; Brian Schar

(57) ABSTRACT

Principles of the present disclosure are directed to novel methods and devices for efficient and targeted delivery of impermeable exogenous materials such as small molecules, proteins, antibodies, and genes into cells, both in vitro as well as in vivo, which is of great importance for drug, vaccine and gene delivery for various therapeutic applications. Specifically, the invention provides device and method for targeted nano-enhanced optical delivery of opsins for vision restoration in patients with retinal photodegeneration by conventional intravitreal/sub-retinal injection of gold nano-rods and opsin plasmids followed by scanned/spatially modulated laser beam matching the pathological areas determined by Fundoscopy, OCT or scanning ophthalmoscope.

17 Claims, 15 Drawing Sheets

(56) References Cited

OTHER PUBLICATIONS

Schomaker, Markus, et. al.; "Characterization of nanoparticle mediated laser transfection by femosecond laser pulses for applications in molecular medicine," Journal of Nanobiotechnology (2015) 13:10; Feb. 3, 2015.
Wang, Bei-Ke, et. al.; "Gold nanorods-siRNA nanoplex for improved photothermal therapy by gene silencing," Biomaterials 78 (2016) 27-39, Nov. 19, 2015.
Japan Office Action Summary, dated Sep. 5, 2019.
Chatrchyan, S. et. al.; "The CMS experiment at the Cern LHC," Journal of Instrumentation, Institute of Physics Publishing, vol. 3, No. 8, Aug. 1, 2008.
International Search Report PCT/US2017/017636 dated Apr. 25, 2017.
Australian office action dated Dec. 2019.
Gu, L., et. al.; "Crystalline magnetic carbon nanoparticle assisted photothermal delivery into cells using CW near-infrared laser beam," Scientific Reports, No. 4, Article: 5106; May 29, 2014.
Kam, N.W.S., et. al.; "Carbon nanotubes as multifunctional biological transporters and near-infrared agents for selective cancer cell destruction," Proceedings of the National Academy of Sciences, vol. 102, No. 33, pp. 11600-11605 (Aug. 16, 2005).
Zufferey R, Nagy D, Mandel R J, Naldini L, Trono D. Multiply attenuated lentiviral vector achieves efficient gene delivery in vivo. Nat Biotech. 1997; 15(9):871-5.
57. Gobin A M, Lee M H, Halas N J, James W D, Drezek R A, West J L. Near-Infrared Resonant Nanoshells for Combined Optical Imaging and Photothermal Cancer Therapy. Nano Letters. 2007; 7(7):1929-34.
Adamantidis A R, Tsai H C, Boutrel B, Zhang F, Stuber G D, Budygin E A, et al. Optogenetic interrogation of dopaminergic modulation of the multiple phases of reward-seeking behavior. J Neurosci. 2011; 31(30):10829-35.
Akilov O E, Wu M X, Jin Y, Zhou Z, Geskin L J, Falo L D, et al. Vaccination with photodynamic therapy-treated macrophages induces highly suppressive T-regulatory cells. Photodermatol, Photoimmunol Photomed. 2011; 27(2):97-107.
Alilain W J, Li X, Horn K P, Dhingra R, Dick T E, Herlitze S, et al. Light-Induced Rescue of Breathing after Spinal Cord Injury. J Neurosci. 2008; 28(46):11862-70.
Baumgartner W A. Etiology, pathogenesis, and experimental treatment of retinitis pigmentosa. Medical Hypotheses. 2000; 54(5):814-24.
Bi A D, Cui J J, Ma Y P, Olshevskaya E, Pu M L, Dizhoor A M, et al. Ectopic expression of a microbial-type rhodopsin restores visual responses in mice with photoreceptor degeneration. Neuron. 2006; 50(1):23-33.
Bi A, Cui J, Ma Y P, Olshevskaya E, Pu M, Dizhoor A M, et al. Ectopic expression of a microbial-type rhodopsin restores visual responses in mice with photoreceptor degeneration. Neuron. 2006; 50(1):23-33.
Biarnes M, Mones J, Alonso J, Arias L. Update on geographic atrophy in age-related macular degeneration. Optom Vis Sci. 2011; 88(7):881-9.
Boyden E S, Zhang F, Bamberg E, Nagel G, Deisseroth K. Millisecond-timescale, genetically targeted optical control of neural activity. Nat Neurosci. 2005; 8(9):1263-8.
Brongersma M L. Nanoscale photonics: Nanoshells: gifts in a gold wrapper. Nat Mater. 2003; 2(5):296-7.
Burridge K, Feramisco J R. Microinjection and localization of a 130K protein in living fibroblasts: a relationship to actin and fibronectin. Cell. 1980; 19(3):587-95.
Busskamp V, Duebel J, Balya D, Fradot M, Viney T J, Siegert S, et al. Genetic Reactivation of Cone Photoreceptors Restores Visual Responses in Retinitis Pigmentosa. Science. 2010; 329(5990):413-7.
Busskamp V, Picaud S, Sahel J A, Roska B. Optogenetic therapy for retinitis pigmentosa; Gene Ther. 2012; 19(2):169-75.

Cao H, Gu L, Mohanty S K, Chiao J C. An Integrated mu LED Optrode for Optogenetic Stimulation and Electrical Recording. Ieee T Bio-Med Eng. 2013; 60(1):225-9.
Chader G J. Animal models in research on retinal degenerations: past progress and future hope. Vision Res. 2002; 42(4):393-9.
Chen J, Saeki F, Wiley B J, Cang H, Cobb M J, Li Z-Y, et al. Gold Nanocages: Bioconjugation and Their Potential Use as Optical Imaging Contrast Agents. Nano Letters. 2005; 5(3):473-7.
Chen J, Wang D, Xi J, Au L, Siekkinen A, Warsen A, et al. Immuno Gold Nanocages with Tailored Optical Properties for Targeted Photothermal Destruction of Cancer Cells. Nano Letters. 2007; 7(5):1318-22.
Cheng Y, Samia A C, Li J, Kenney M E, Resnick A, Burda C. Delivery and efficacy of a cancer drug as a function of the bond to the gold nanoparticle surface. Langmuir. 2010; 26(4):2248-55.
Curcio C A, Medeiros N E, Millican C L. Photoreceptor loss in age-related macular degeneration. Invest Ophthalmol Vis Sci. 1996; 37(7):1236-49.
Daiger S P, Bowne S J, Sullivan L S. Perspective on genes and mutations causing retinitis pigmentosa. Arch Ophthalmol. 2007; 125(2):151-8.
Deisseroth K. Optogenetics. Nat Meth. 2011; 8(1):26-9.
Dhakal K, Black B, Mohanty S. Introduction of impermeable actin-staining molecules to mammalian cells by optoporation. Sci Rep. 2014; 4(6553):1-7.
Dhakal K, Gu L, Shivalingaiah S, Dennis T, Bobzean S, Perrotti L, et al. Non-scanning fiber-optic near-infrared beam led to two-photon optogenetic stimulation in vivo. Plos One. 2014; in press.
Dichtl A, Jonas J B, Naumann G O. Retinal nerve fiber layer thickness in human eyes; Graefe's archive for clinical and experimental ophthalmology. 1999; 237(6):474-9.
Doroudchi M M, Greenberg K P, Liu J, Silka K A, Boyden E S, Lockridge J A, et al. Virally delivered Channelrhodopsin-2 Safely and Effectively Restores Visual Function in Multiple Mouse Models of Blindness. Mol Ther. 2011; 19(7):1220-9.
Editorial, Method of the Year 2010. Nat Meth. 2011; 8(1):1-.
Fehrentz T, Schonberger M, Trauner D. Optochemical genetics. Angew Chem Int Ed Engl. 2011; 50(51):12156-82.
Fenno L, Yizhar O, Deisseroth K. The Development and Application of Optogenetics. Ann Rev Neurosci. 2011; 34(1):389-412.
Ferber D. Safer and Virus-Free? Science. 2001; 294(5547):1638-42.
Fernandez de Castro J P, Scott P A, Fransen J W, Demas J, DeMarco P J, Kaplan H J, et al. Cone photoreceptors develop normally in the absence of functional rod photoreceptors in a transgenic swine model of retinitis pigmentosa. Invest Ophthalmol Vis Sci. 2014; 55(4):2460-8.
Flannery J G, Farber D B, Bird A C, Bok D. Degenerative changes in a retina affected with autosomal dominant retinitis pigmentosa. Invest Ophthalmol Vis Sci. 1989; 30(2):191-211.
Fleckenstein M, Schmitz-Valckenberg S, Adrion C, Kramer I, Eter N, Helb H M, et al. Tracking progression with spectral-domain optical coherence tomography in geographic atrophy caused by age-related macular degeneration. Invest Ophthalmol Vis Sci. 2010; 51(8):3846-52.
Grover S, Fishman G A, Anderson R J, Alexander K R, Derlacki D J. Rate of visual field loss in retinitis pigmentosa. Ophthalmology. 1997; 104(3):460-5.
Grunwald J E, Pistilli M, Ying G S, Maguire M G, Daniel E, Martin D F. Growth of Geographic Atrophy in the Comparison of Age-related Macular Degeneration Treatments Trials. Ophthalmology. 2014.
Gu L, Mohanty S K. Targeted microinjection into cells and retina using optoporation. J Biomed Opt. 2011; 16(12):128003-6.
Hamel C. Retinitis pigmentosa. Orphanet J Rare Dis. 2006; 1:40.
Han X, Boyden E S. Multiple-Color Optical Activation, Silencing, and Desynchronization of Neural Activity, with Single-Spike Temporal Resolution. PLoS ONE. 2007; 2(3):e299.
Hartong D T, Berson E L, Dryja T P. Retinitis pigmentosa. Lancet. 2006; 368(9549):1795-809.
Hosokawa Y, Iguchi S, Yasukuni R, Hiraki Y, Shukunami C, Masuhara H. Gene delivery process in a single animal cell after femtosecond laser microinjection. Appl Surf Sci. 2009; 255(24):9880-4.

(56) References Cited

OTHER PUBLICATIONS

Huang X, El-Sayed I H, Qian W, El-Sayed M A. Cancer Cell Imaging and Photothermal Therapy in the Near-Infrared Region by Using Gold Nanorods. Journal of the American Chemical Society. 2006; 128(6):2115-20.
Ishikawa Y, Mine S. Aminoadipic Acid Toxic Effects on Retinal Glial-Cells. Jpn J Ophthalmol. 1983; 27(1):107-18.
Ivanova E, Roberts R, Bissig D, Pan Z-H, Berkowitz B A. Retinal channelrhodopsin-2-mediated activity in vivo evaluated with manganese-enhanced magnetic resonance imaging. J Molecular Vision. 2010; 16:1059-67.
Jacobson S G, Roman A J, Aleman T S, Sumaroka A, Herrera W, Windsor E A, et al. Normal central retinal function and structure preserved in retinitis pigmentosa. Invest Ophthalmol Vis Sci. 2010; 51(2):1079-85.
Johansen J P, Hamanaka H, Monfils M H, Behnia R, Deisseroth K, Blair H T, et al. Optical activation of lateral amygdala pyramidal cells instructs associative fear learning. Proc Nat Acad Sci. 2010; 107(28):12692-7.
Kamimura K, Suda T, Zhang G, Liu D. Advances in Gene Delivery Systems. Pharmaceut. Med. 2011; 25(5):293-306.
Kavalali E T, Jorgensen E M. Visualizing presynaptic function. Nat Neurosci. 2014; 17(1):10-6.
Kim B, Han G, Toley B J, Kim C-k, Rotello V M, Forbes N S. Tuning payload delivery in tumour cylindroids using gold nanoparticles Nat Nano. 2010; 5(6):465-72.
King R. Gene Delivery to Mammalian Cells by Microinjection. Methods in Molecular Biology. 2004; 245(2):167-73.
Klein M L, Ferris F L, 3rd, Francis P J, Lindblad A S, Chew E Y, Hamon S C, et al. Progression of geographic atrophy and genotype in age-related macular degeneration. Ophthalmology. 2010; 117(8):1554-9, 9 e1.
Koizumi A, Tanaka K F, Yamanaka A. The manipulation of neural and cellular activities by ectopic expression of melanopsin. Neurosci Res. 2013; 75(1):3-5.
Kraszewski K, Mundigl O, Daniell L, Verderio C, Matteoli M, De Camilli P. Synaptic vesicle dynamics in living cultured hippocampal neurons visualized with CY3-conjugated antibodies directed against the lumenal domain of synaptotagmin. J Neurosci. 1995; 15(6):4328-42.
Lagali P S, Balya D, Awatramani G B, Munch T A, Kim D S, Busskamp V, et al. Light-activated channels targeted to ON bipolar cells restore visual function in retinal degeneration. Nat Neurosci. 2008; 11(6):667-75.
Li S, Huang L. Nonviral gene therapy: promises and challenges. Gene Ther. 2000; 7(1):31-4.
Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.
Luo D, Saltzman W M. Synthetic DNA delivery systems. Nat Biotech. 2000; 18(1):33-7.
Mezer E, Babul-Hirji R, Wise R, Chipman M, DaSilva L, Rowell M, et al. Attitudes Regarding Predictive Testing for Retinitis Pigmentosa. Ophthalmic Genetics. 2007; 28(1):9-15.
Miller G. Shining New Light on Neural Circuits. Science. 2006; 314(5806):1674-6.
Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.
Mohanty S K, Sharma M, Gupta P K. Laser-assisted microinjection into targeted animal cells. Biotech Lett. 2003; 25(11):895-9.
Nagel G, Brauner M, Liewald J F, Adeishvili N, Bamberg E, Gottschalk A. Light activation of channelrhodopsin-2 in excitable cells of Caenorhabditis elegans triggers rapid behavioral responses. Curr Biol. 2005; 15(24):2279-84.
Nagel G, Szellas T, Huhn W, Kateriya S, Adeishvili N, Berthold P, et al. Channelrhodopsin-2, a directly light-gated cation-selective membrane channel. Proc Nat Acad Sci. 2003; 100(24):13940-5.
Naldini L, Blomer U, Gallay P, Ory D, Mulligan R, Gage F H, et al. In Vivo Gene Delivery and Stable Transduction of Nondividing Cells by a Lentiviral Vector. Science. 1996; 272(5259):263-7.
Newman C M, Lawrie A, Brisken A F, Cumberland D C. Ultrasound Gene Therapy: On the Road from Concept to Reality. Echocardiography. 2001; 18(4):339-47.
Office Action, dated May 2020, JP2018-543151.
Palumbo G, Caruso M, Crescenzi E, Tecce M F, Roberti G, Colasanti A. Targeted gene transfer in eucaryotic cells by dye-assisted laser optoporation. J Photochem Photobiol B. 1996; 36(1):41-6.
Panyam J, Labhasetwar V. Biodegradable nanoparticles for drug and gene delivery to cells and tissue. Adv Drug Deliv Rev. 2003; 55(3):329-47.
Pastrana E. Optogenetics: controlling cell function with light. Nat Meth. 2011; 8(1):24-5.
Pedersen O O, Karlsen R L. Destruction of Muller cells in the adult rat by intravitreal injection of D,L-alpha-aminoadipic acid. An electron microscopic study. Exp Eye Res. 1979; 28(5):569-75.
Ruitenberg M J, Eggers R, Boer G J, Verhaagen J. Adeno-associated viral vectors as agents for gene delivery: application in disorders and trauma of the central nervous system. Methods. 2002; 28(2):182-94.
Sahaboglu A, Paquet-Durand O, Dietter J, Dengler K, Bernhard-Kurz S, Ekstrom P A, et al.; Retinitis pigmentosa: rapid neurodegenration is governed by slow cell death mechanisms. Cell Death Dis. 2013; 4:e488.
Schinkel H, Jacobs P, Schillberg S, Wehner M. Infrared picosecond laser for perforation of single plant cells. Biotechnol Bioeng. 2008; 99(1):244-8.
Schneckenburger H, Hendinger A, Sailer R, Strauss W S, Schmitt M. Laser-assisted optoporation of single cells. J Biomed Opt. 2002; 7(3):410-6.
Schroll C, Riemensperger T, Bucher D, Ehmer J, Voller T, Erbguth K, et al. Light-induced activation of distinct modulatory neurons triggers appetitive or aversive learning in *Drosophila larvae*. Current Biology. 2006; 16(17):1741-7.
Shivalingaiah S, Gu L, Mohanty S K. Correlation of spatial intensity distribution of light reaching the retina and restoration of vision by optogenetic stimulation. Proc SPIE. 2011; 7885:78851Y.
Shivalingaiah S, Gu L, Mohanty S K. Non-linear stimulation of excitable cells with and without optogenetic sensitization. Proc SPIE 2011; 7883:788355.
Somia N, Verma I M. Gene therapy: trials and tribulations. Nat Rev Genet. 2000; 1(2):91-9.
Stracke F, Rieman I, Konig K. Optical nanoinjection of macromolecules into vital cells; Journal of Photochemistry and Photobiology B: Biology. 2005; 81(3):136-42.
Sugano E, Isago H, Wang Z, Murayama N, Tamai M, Tomita H. Immune responses to adeno-associated virus type 2 encoding channelrhodopsin-2 in a genetically blind rat model for gene therapy. Gene Ther. 2011; 18(3):266-74.
Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.
Sunness J S, Applegate C A, Bressler N M, Hawkins B S. Designing clinical trials for age-related geographic atrophy of the macula: enrollment data from the geographic atrophy natural history study. Retina. 2007; 27(2):204-10.
Sunness J S, Margalit E, Srikumaran D, Applegate C A, Tian Y, Perry D, et al. The long-term natural history of geographic atrophy from age-related macular degeneration: enlargement of atrophy and implications for interventional clinical trials. Ophthalmology. 2007; 114(2):271-7.
Tao W, Wilkinson J, Stanbridge E J, Berns M W. Direct gene transfer into human cultured cells facilitated by laser micropuncture of the cell membrane. Proc Natl Acad Sci USA. 1987; 84(12):4180-4.

(56) References Cited

OTHER PUBLICATIONS

Templeton N S, Lasic D D, Frederik P M, Strey H H, Roberts D D, Pavlakis G N. Improved DNA: liposome complexes for increased systemic delivery and gene expression. Nat Biotech. 1997; 15(7):647-52.

Thomas C E, Ehrhardt A, Kay M A. Progress and problems with the use of viral vectors for gene therapy. Nat Rev Genet. 2003; 4(5):346-58.

Thyagarajan S, van Wyk M, Lehmann K, Lowel S, Feng G, Wassle H. Visual Function in Mice with Photoreceptor and Degeneration Transgenic Expression of Channelrhodopsin 2 in Ganglion Cells. J Neurosci. 2010; 30(26):8745-58.

Tirlapur U K, Konig K. Femtosecond near-infrared laser pulses as a versatile non-invasive tool for intra-tissue nanoprocessing in plants without compromising viability. Plant J. 2002; 31(3):365-74.

Tirlapur U K, Konig K. Targeted transfection by femtosecond laser. Nature. 2002; 418(6895):290-1.

Tomita H, Sugano E, Fukazawa Y, Isago H, Sugiyama Y, Hiroi T, et al. Visual Properties of Transgenic Rats Harboring the Channelrhodopsin-2 Gene Regulated by the Thy-1.2 Promoter. PLoS One. 2009; 4(11).

Tomita H, Sugano E, Isago H, Hiroi T, Wang Z, Ohta E, et al. Channelrhodopsin-2 gene transduced into retinal ganglion cells restores functional vision in genetically blind rats. Experimental Eye Research. 2010; 90(3):429-36.

Tong L, Zhao Y, Huff T, Hansen M, Wei A, Cheng J X. Gold Nanorods Mediate Tumor Cell Death by Compromising Membrane Integrity. Advanced Materials. 2007; 19(20):3136-41.

Tonnesen J, Parish C L, Sorensen A T, Andersson A, Lundberg C, Deisseroth K, et al.; Functional Integration of Grafted Neural Stem Cell-Derived Dopaminergic Neurons Monitored by Optogenetics in an In Vitro Parkinson Model. PLoS ONE. 2011; 6(3):e17560.

Tsien R Y. The Gree Fluorescent Protein. Ann Rev Biochem. 1998; 67(1):509-44.

Verma I M, Somia N. Gene therapy—promises, problems and prospects. Nature 1997; 389(6648):239-42.

Wallsh J, Gallemore R. Optical coherence tomography difference maps and average macular volume for geographic atrophy. Retin Cases Brief Rep. 2015; 9(1):88-91.

Wang S, Chen K J, Wu T H, Wang H, Lin W Y, Ohashi M, et al. Photothermal Effects of Supramolecularly Assembled Gold Nanoparticles for the Targeted Treatment of Cancer Cells. Angewandte Chemie. 2010; 122(22):3865-9.

Wu Z, Ayton L N, Luu C D, Guymer R H. Microperimetry of nascent geographic atrophy in age-related macular degeneration. Invest Ophthalmol Vis Sci. 2015; 56(1):115-21.

Yu J-Y, DeRuiter S L, Turner D L. RNA interference by expression of short-interfering RNAs and hairpin RNAs in mammalian cells. Proc Nat Acad Sci. 2002; 99(9):6047-52.

Zhang F, Aravanis A M, Adamantidis A, de Lecea L, Deisseroth K. Circuit-breakers: optical technologies for probing neural signals and systems. Nat Rev Neurosci. 2007; 8(8):577-81.

Zhang F, Wang L P, Boyden E S, Deisseroth K. Channelrhodopsin-2 and optical control of excitable cells. Nat Methods. 2006; 3(10):785-92.

Zhang Y, Ivanova E, Bi A, Pan Z-H. Ectopic Expression of Multiple Microbial Rhodopsins Restores O N and OFF Light Responses in Retinas with Photoreceptor Degeneration. J Neurosci. 2009; 29(29):9186-96.

\* cited by examiner

Fig. 3A
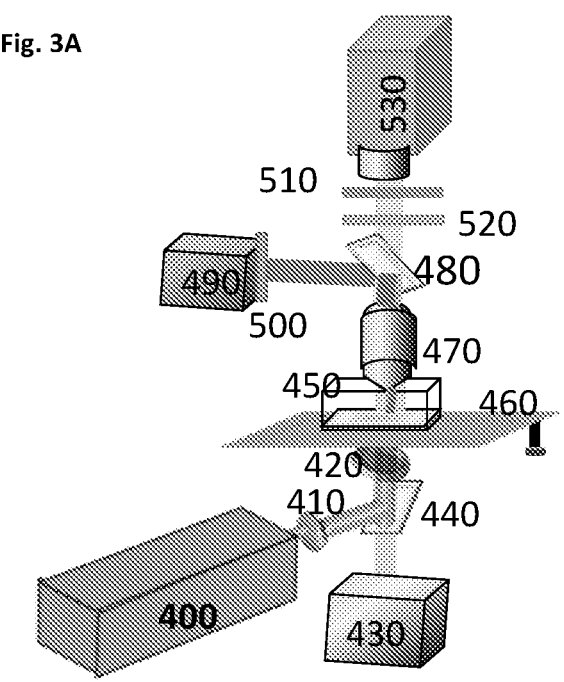
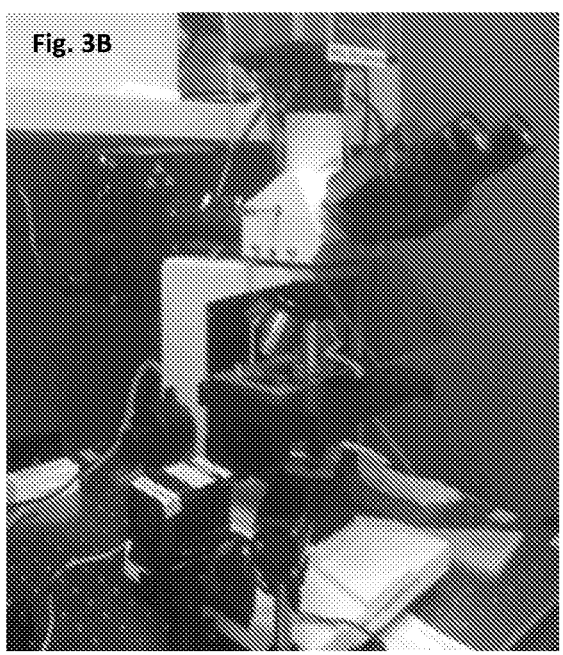
Fig. 3B

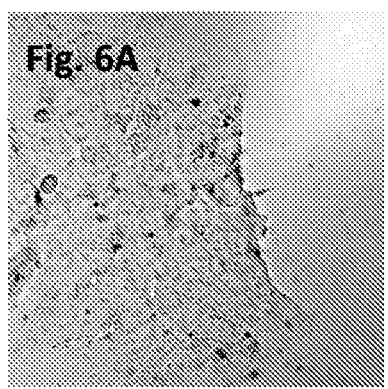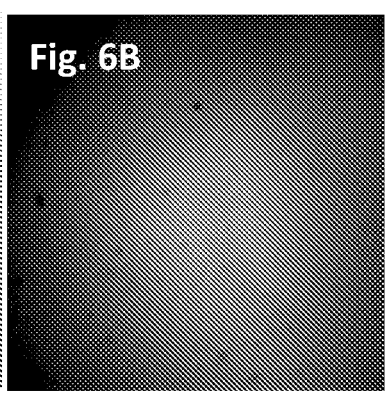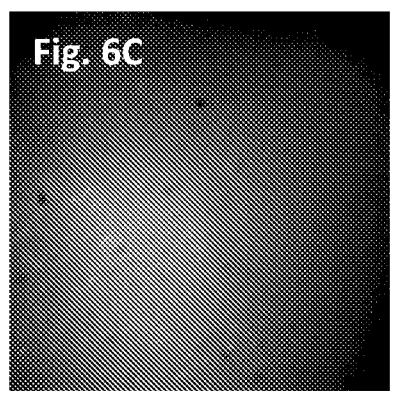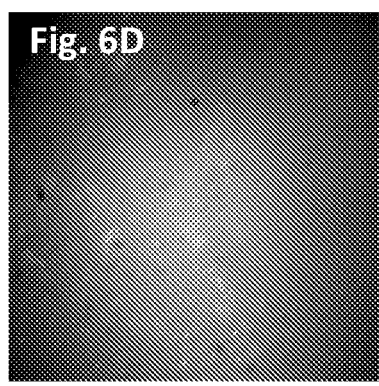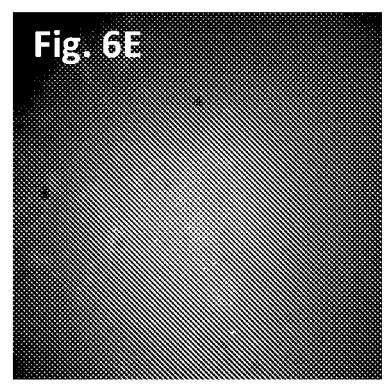
Fig. 6

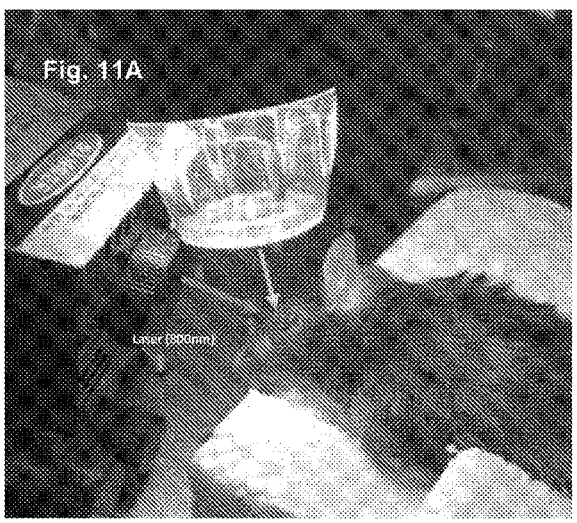
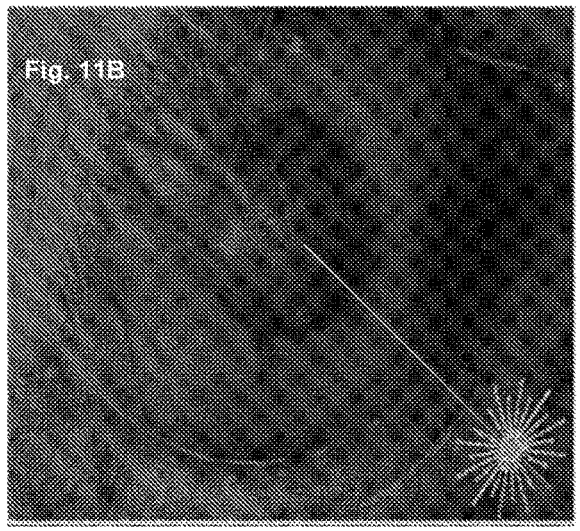
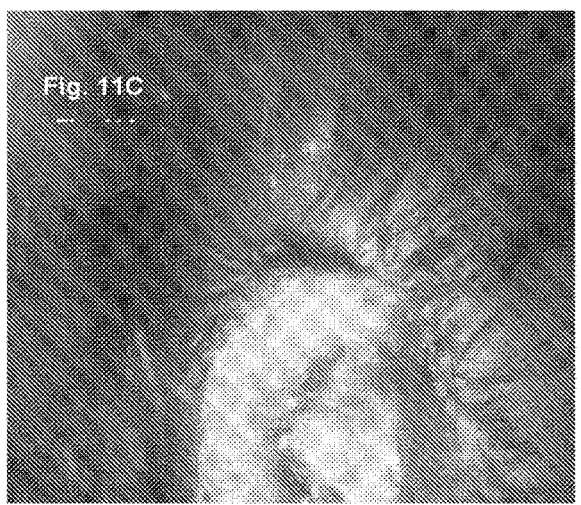
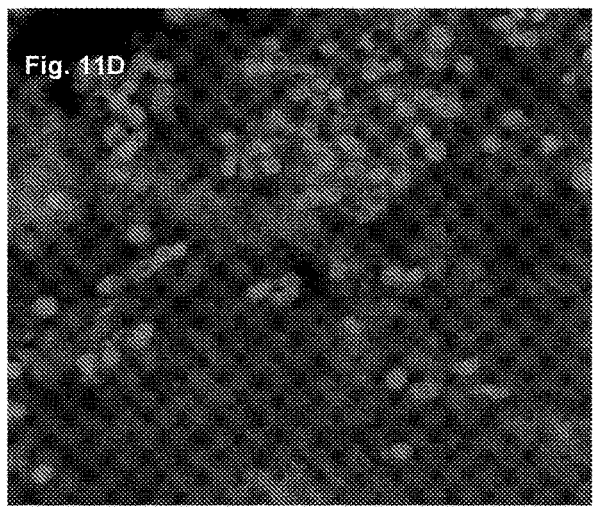

NANO-ENHANCED OPTICAL DELIVERY OF EXOGENOUS MOLECULES TO CELLS AND TISSUES

CROSS-REFERENCE

This application claims the benefit of U.S. provisional application No. 62/295,030 filed Feb. 13, 2016, which application is incorporated herein by reference.

STATEMENT REGARDING FEDERALLY SPONSORED RESEARCH OR DEVELOPMENT

This invention was made primarily with funding by NanoScope Technologies, LLC as well as US. Government support under the National Institutes of Health/National Eye Institute grant (1R43EY026483-01). The Government has certain rights in the invention.

FIELD OF THE INVENTION

The present disclosure relates generally to devices and methods for efficient and targeted delivery of impermeable exogenous materials (such as small molecules, nucleic acids, proteins, antibodies, and genes) into cells, both in vitro as well as in vivo, and is of great importance for drug, vaccine and gene delivery for therapeutic strategies.

The present disclosure is directed to novel method and systems for cell-specific spatially targeted delivery of impermeable agents, such as, but not limited to labeling or therapeutic agents. Further, the disclosure provides devices and methods for targeted optical delivery of opsins for vision restoration in patients with retinal photodegeneration by conventional intravitreal injection of nanoparticles, such as but not limited to, gold nano-rods, and opsin plasmids.

BACKGROUND OF THE INVENTION

The introduction of foreign DNA (1), short-interfering RNA (2), small molecules, proteins (3) and drugs into living cells, organs and whole organisms is essential for a variety of applications in genetics, cell and developmental biology, vaccination (4), gene therapy (5, 6) and other therapeutic strategies. Further, the transfection of plasmids encoding fluorescent proteins (7) is routinely used to visualize cellular and sub-cellular structures and also to study various functional aspects of cell and developmental biology (8). Further, by targeted delivery of genes coded for light-sensitive opsins, selected groups of excitable cells (neuronal, muscle, cardiac, etc) can be specifically stimulated or silenced with high temporal precision by low-power light (9-12). This optogenetics (13-18) approach has heavily impacted neuroscience by allowing dissection of neuronal circuitry, which may prove valuable in the treatment of several neurological disorders (19-25). However, the complexity of existing delivery systems poses a major obstacle (6) in translating gene therapy methods into clinical practice.

SUMMARY OF THE INVENTION

To meet the challenges in spatially targeted delivery of impermeable molecules to cells and tissues, principles of the present disclosure provide a nano-enhanced optical method to achieve targeted delivery into cells in-vitro as well as in-vivo in the skin and retina using a low power near-infrared laser beam for different uses including vision restoration. The invention also includes several devices for targeted delivery including scanning of the beam, shaping the beam, and achieving wave front-correction.

In addition, the invention in some aspects provides integrated nano-enhanced optical delivery (NOD) device with fundoscopy, scanning laser ophthalmoscopy, and Optical coherence tomography to identify targeted region requiring delivery of therapeutic molecules.

This invention demonstrates that plasmids and impermeable substances can be introduced into cells in a minimally invasive manner by nano-enhanced photothermal means using a continuous wave (cw) near-infrared (NIR) laser beam. In this Nano-enhanced Optical Delivery (NOD) method, the NIR field enhancement by gold nano-rods (GNR) is utilized to transiently perforate cell membrane to deliver exogenous molecules to cells via hot spots at the end of the rods. Spatially targeted in-situ delivery is achieved by shining the continuous wave (cw) NIR laser beam in targeted areas. The NOD method shows that impermeable opsin-plasmids are delivered into targeted cells using near-IR (NIR) continuous wave laser beam.

According to another aspect of the invention, the disclosed invention provides method for the use of NOD method to deliver opsins for vision restoration and other applications. The efficient localized photothermal conversion by gold nanostructures (52-60) in the safe NIR spectrum allowed in vivo nano-enhanced optical delivery (NOD) of opsin-plasmids into cells in targeted regions of photodegenerated retina in animal models.

The results clearly demonstrate that the proposed NOD is a viable, non-invasive approach to remotely guide delivery of exogenous molecules to targeted cells. Since the gold nano-structures have very low cytotoxicity and have been widely used in various clinical trials, it is an ideal nanomaterial for clinical translation of the NOD method. Compared with pulsed lasers, cw NIR (diode) lasers are compact, easy-to-use and therefore, have significant translational potential. For example, targeted in-vivo optical delivery of opsin genes to degenerated retinal regions in dry-AMD patients using near-infrared laser beam in a safe manner will enable restoration of photosensitivity in the geographic atrophy areas.

In one aspect, the disclosure provides mechanism of the NOD approach, where the contrast in temperature rise in laser-irradiated nano-rod-attached cells versus surrounding cells is significant enough to allow site-specific delivery of plasmids. In one embodiment, principles of the present disclosure provide methods and devices for cell specific delivery of an agent of interest. The method includes delivery of a first agent to a first cell type and delivery of a second agent to a second cell type. In some embodiments delivery occurs in vitro but in other embodiments delivery occurs in vivo.

The present disclosure provides a method of delivering opsin-genes to photodegenerated retinas in order to restore light sensitivity. The results presented herein show efficient and stable in-vivo expression of opsin-reporter protein in mice retina after intravitreal injection of gold nano-rods and opsin-plasmids, followed by Nano-enhanced optical delivery.

According to yet another aspect, the present disclosure provides a method of restoration of vision in human having geographic atrophies in retina. The method include delivery of the opsin-genes to spatially-targeted retinal cells in-vivo by NOD in the eye, and/or in combination with Alpha-Aminoadipic Acid (AAA) for enhancing delivery efficiency to targeted retinal layer crossing the thick inner limiting membrane in humans. Safe NOD-mediated opsin-delivery has potential for effective gene therapy of diverse retinal degenerations in patients.

The disclosure provides a method, wherein cells have been contacted with or comprises gold nanostructures and nucleic acid molecule that encodes for an opsin. Preferably, the cells in retina are ON-type ganglion cells, or ON-type bipolar cells.

In a broader aspect, the disclosure provides methods for delivering diagnostic and therapeutic molecules to modulate the cell and tissue function, and for use in diagnosis and treatment of disorders.

It is contemplated that any embodiment of a method or composition described herein can be implemented with respect to any other method or composition described herein.

Details associated with the embodiments described above and others are described below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

100: identify target population of cells;
110: Add gold nanorods functionalized for specific cells,
120: Functionalized gold nanorods binds to targeted cells,
130: Add molecules to-be-delivered into the medium,
140: Irradiate with CW laser tuned to SPR of nanorods,
150: Molecules enter via membrane exposed to hotspots,
160: Molecules continue to enter via membrane exposed to hotspots just after switching off the laser,
170: Injected molecules bind to targeted oranelles
180: Wash unbound rods and molecules,
190: Add gold nanorods of different shape functionalized for next group of cells,
200: Functionalized nanorods binds to next group of targeted cells, 210: Add new molecules to-be-delivered into the medium,
220: Irradiate with new SPR-matched laser beam,
230: New molecules enter into next group of cells via hotspots,
240: Injected new molecules bind with targeted organelles in $2^{nd}$ group of cells.

Figure 2A:
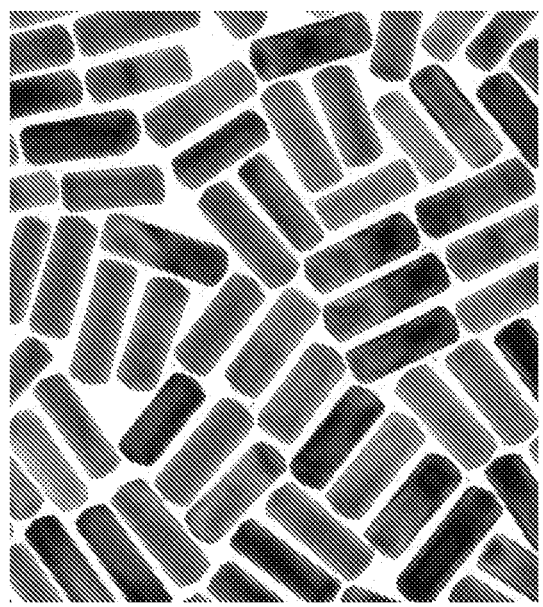
Figure 2B:
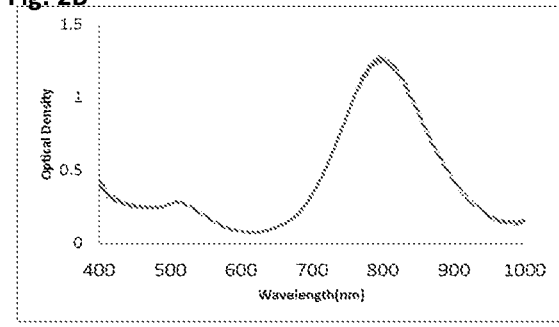
Figure 2C:
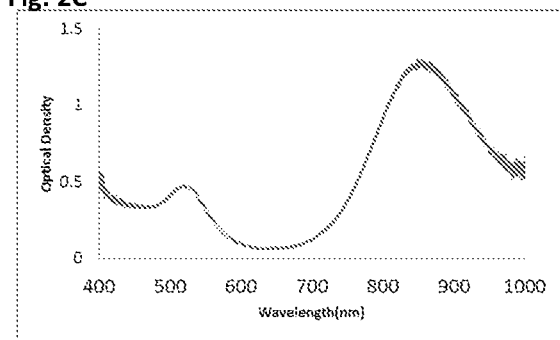

FIG. 2A shows High magnification electron microscopic image of gold nano-rods used for optical enhancement of laser beam (hot spots) at the ends of the rods. These nano-rods are functionalized with PEG, Concanavalin A or Antibodies for target-specific binding to different types of cells. FIG. 2B shows measured optical density of type1 gold nano-rods showing peak at 800 nm. FIG. 2C shows the optical density of type 2 gold nano-rods showing peak at 850 nm.

FIG. 3A shows Schematic of set up for nano-enhanced optical delivery into cells in-vitro and in-vivo. 400=CW Laser; 410=Focusing Lens; 420=Condenser Lens; 430=White light; 440=Dichroic mirror 1; 450=Sample chamber; 460=XY stage; 470=Microscope Objective; 480=Dichroic mirror 2; 490=Fluorescence excitation; 500=Excitation filter; 510=Emission Filter; 520=Laser cut-off Filter; 530=Camera. FIG. 3B shows the picture of the laser coupled upright fluorescence microscope for nano-enhanced optical delivery into cells in-vitro and in-vivo.

Figure 4:
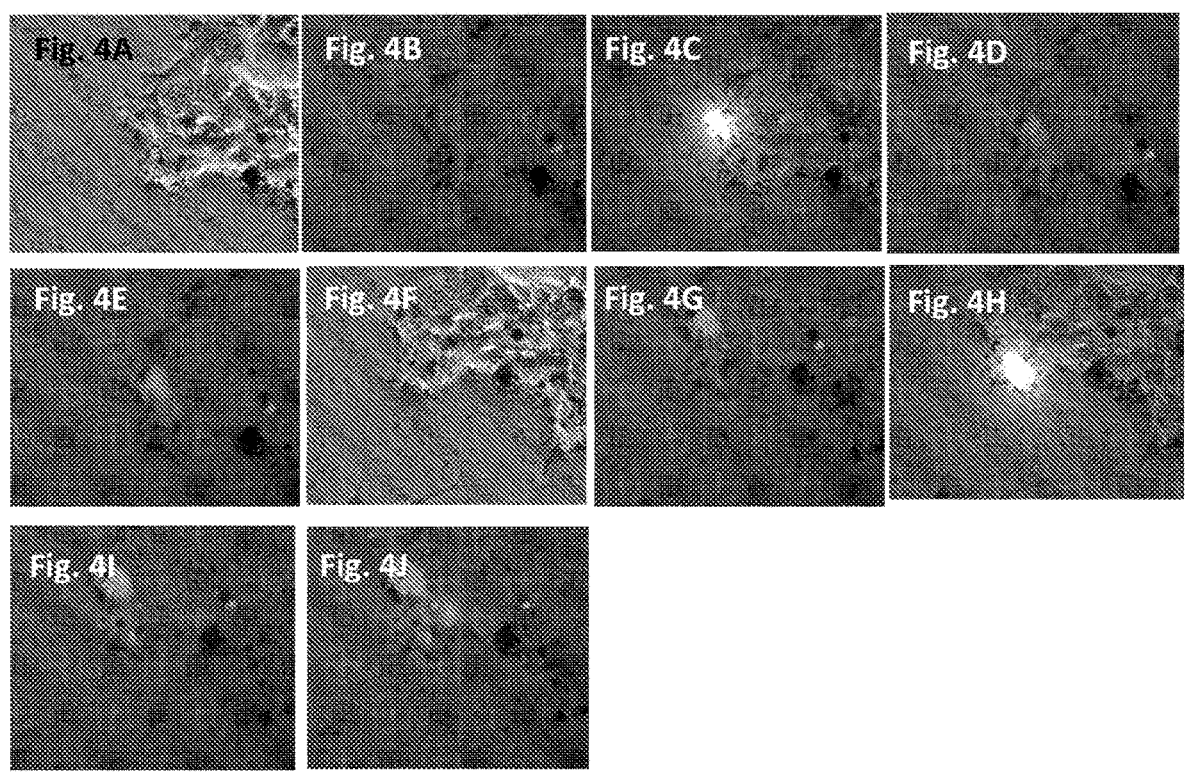

FIG. 4 shows use of gold nano-spheres and green laser beam (532 nm) for delivery of exogenous molecules. FIG. 4A. Bright field image of HEK cells, FIG. 4B. fluorescence image before green laser beam irradiation, FIG. 4C. Green laser beam targeted to localized to a cell, FIG. 4D-FIG. 4E. increase in fluorescence indicating influx of exogenous molecule (Propidium Iodide, PI). FIG. 4F. Brightfield image after XY-movement of sample stage to allow delivery into different cells/region. FIG. 4G. epifluorescence image after sample repositioning, FIG. 4H. Near infrared cw laser irradiation. FIG. 4I-FIG. 4J. rise in fluorescence indicating influx of exogenous molecule (PI) in new targeted cell(s). Besides low penetration depth of green light in biological tissue, severe concerns (cell damage) remain on use of green laser in retina for NOD requiring near-infrared based approach.

Figure 5:
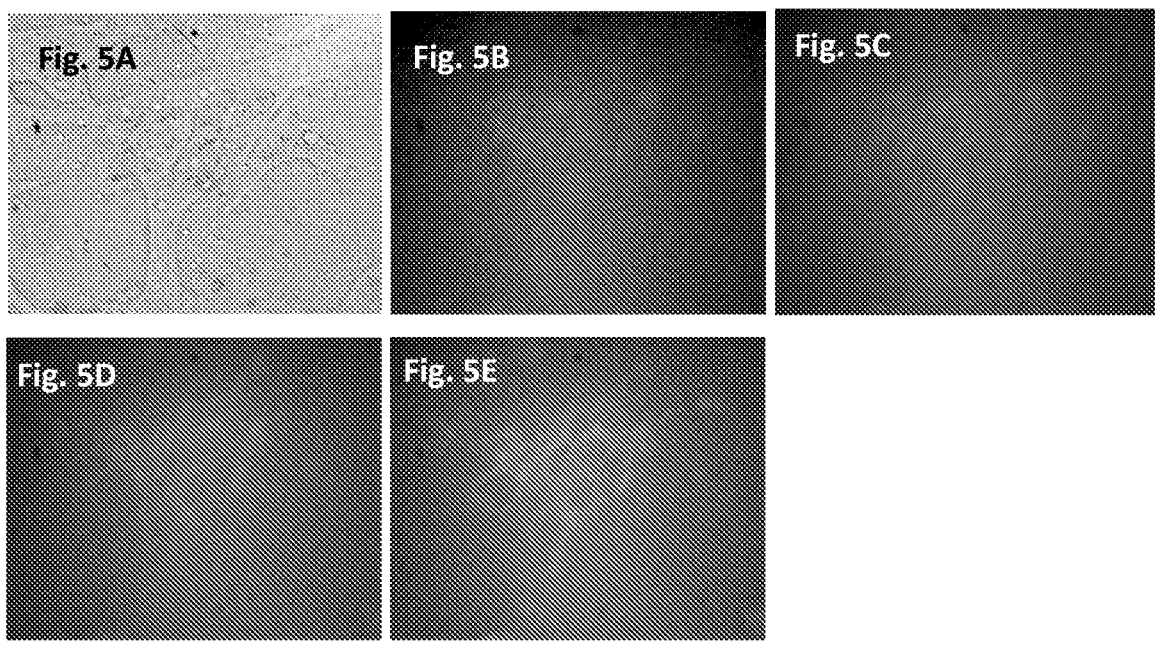

FIG. 5 shows an example of use of gold nano-rods and NIR laser beam (800 nm) for delivery of exogenous impermeably dye molecules into HEK cells. FIG. 5A. Cells attached to functionalized gold nanorods, FIG. 5B. fluorescence before NOD. FIG. 5C-FIG. 5E. Increase in fluorescence intensity and cellular distribution observed after wide-area irradiation by cw NIR laser beam (800 nm) in presence of impermeable actin-staining molecules (Alexa 488 Phalloidin).

FIG. 6 illustrates the use of gold nano-rods and NIR laser beam (800 nm) for delivery of exogenous impermeable antibodies into HEK cells. FIG. 6A. HEK cells attached to functionalized gold nanorods (SPR peak at 800 nm), FIG. 6B. fluorescence before NOD. FIG. 6C to FIG. 6D to FIG. 6E. Increase in intracellular fluorescence intensity (suggesting antibody delivery) observed after wide-area irradiation by cw NIR laser beam (800 nm). Use of wavelength-detuned laser beam (850 nm) did not lead to nano-enhanced optical delivery into the gold nanorod-attached cells.

Figure 7:
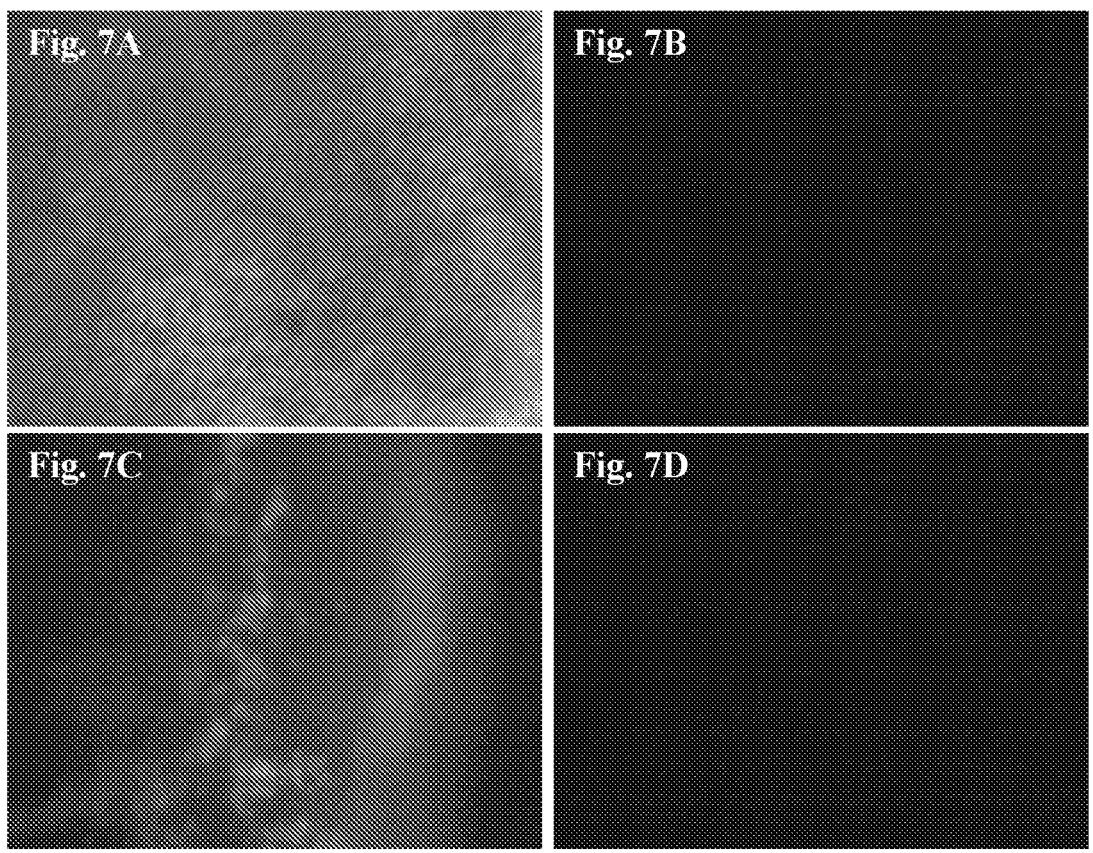

FIG. 7 illustrates the use of gold nano-rods and NIR laser beam for delivery of exogenous impermeable dye molecules into retinal cells in an explant. FIG. 7A. Bright filed image of a retinal explant. Fluorescence image; FIG. 7B, before and FIG. 7C, after exposure of laser (30 sec) in presence of GNR. FIG. 7D: Absence of fluorescence after 30 sec laser exposures in a retinal explant without GNR.

Figure 8A:
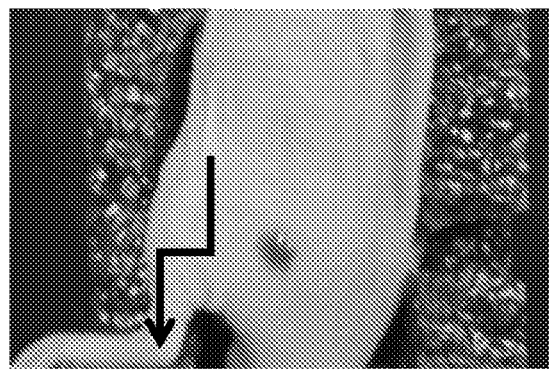
Figure 8B:
Figure 8C:
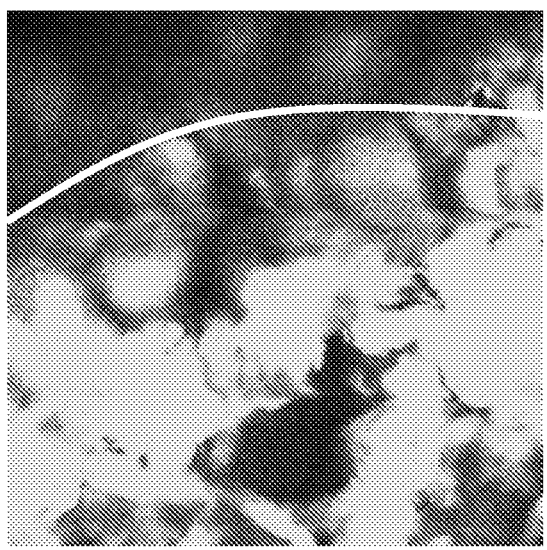

FIG. 8A, FIG. 8B and FIG. 8C illustrate in-vivo gene delivery in skin using NOD. FIG. 8A: A drop of mixture of nanoparticles and GFP plasmids injected in the skin of nude mouse (marked by arrow). FIG. 8B: Targeted irradiation with cw NIR laser beam (800 nm) for NOD. FIG. 8C: GFP expression in NOD region versus neighboring control region (separated by the white line).

Figure 9:
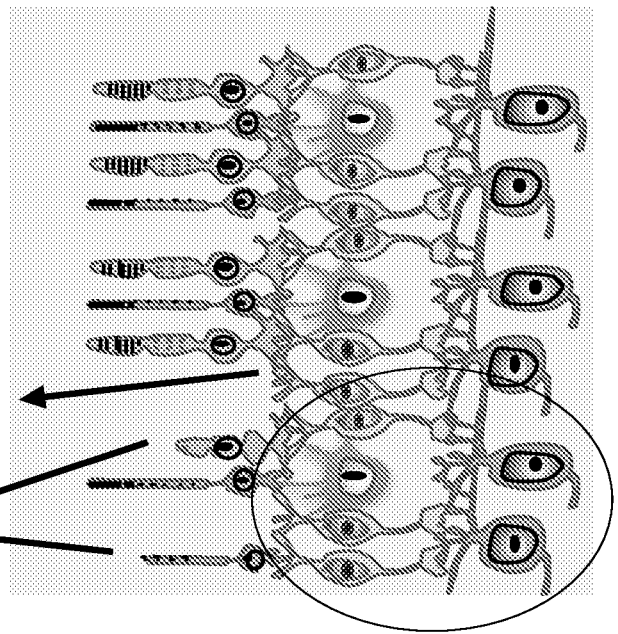

FIG. 9 represents a schematic of the retina showing loss of photoreceptors (Rod, cone) in the encircled region of the retina. Different cellular layers of retina in this targeted photodegenerated region can be microinjected with exogenous therapeutic molecules by NOD-based controlled delivery.

Figure 10:
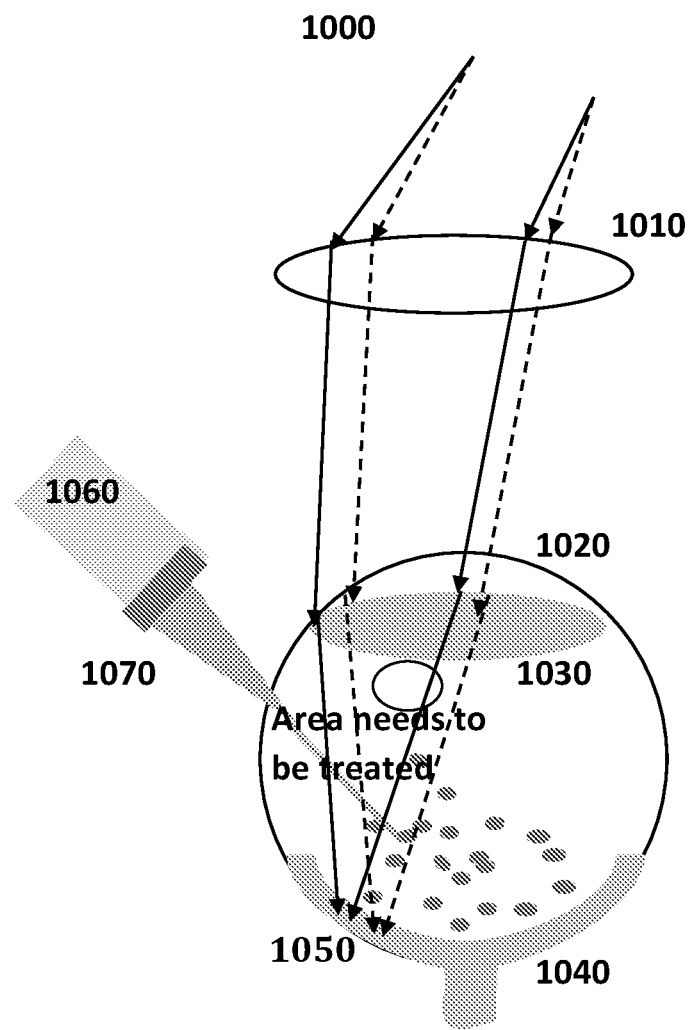

FIG. 10 shows schematic of NOD-based controlled molecular delivery in targeted regions of retina. 1000: NIR laser for NOD; 1010: Optics for correcting beam distorted by cornea (1020) and lens (1030) to focus on retina (1040). 1050: Area needs to be treated; 1060: Gold nanorods and molecules to-be-injected; 1070: injector. The molecules (e.g., genes) injected into the vitreous through sclera. When a near-infrared (NIR) laser irradiates targeted regions of retina (circle), membrane of retinal cells bound with appropriate nano-rod(s) gets permeabilized for exogenous impermeable molecules (e.g. genes). The in-vivo gene delivery system consists of external optics for correcting beam propagation through cornea and lens in the eye to allow irradiation of spatially targeted regions of retina to be delivered with exogenous molecules.

FIG. 11A depicts in-vivo experimental set up for NOD in eye. To minimize non-specific binding, the gold nano-rods are PEGylated. The PEGylation also prevents the aggregation of the gold nano-rods in the vitreous. FIG. 11B shows pupil dilation imaged by laser scanning microscopy. FIG. 11C shows the zoomed image of eye during the laser exposure to near-infrared laser beam. FIG. 11D shows in-vivo expression of Opsin in retina cells in targeted region.

Figure 12:
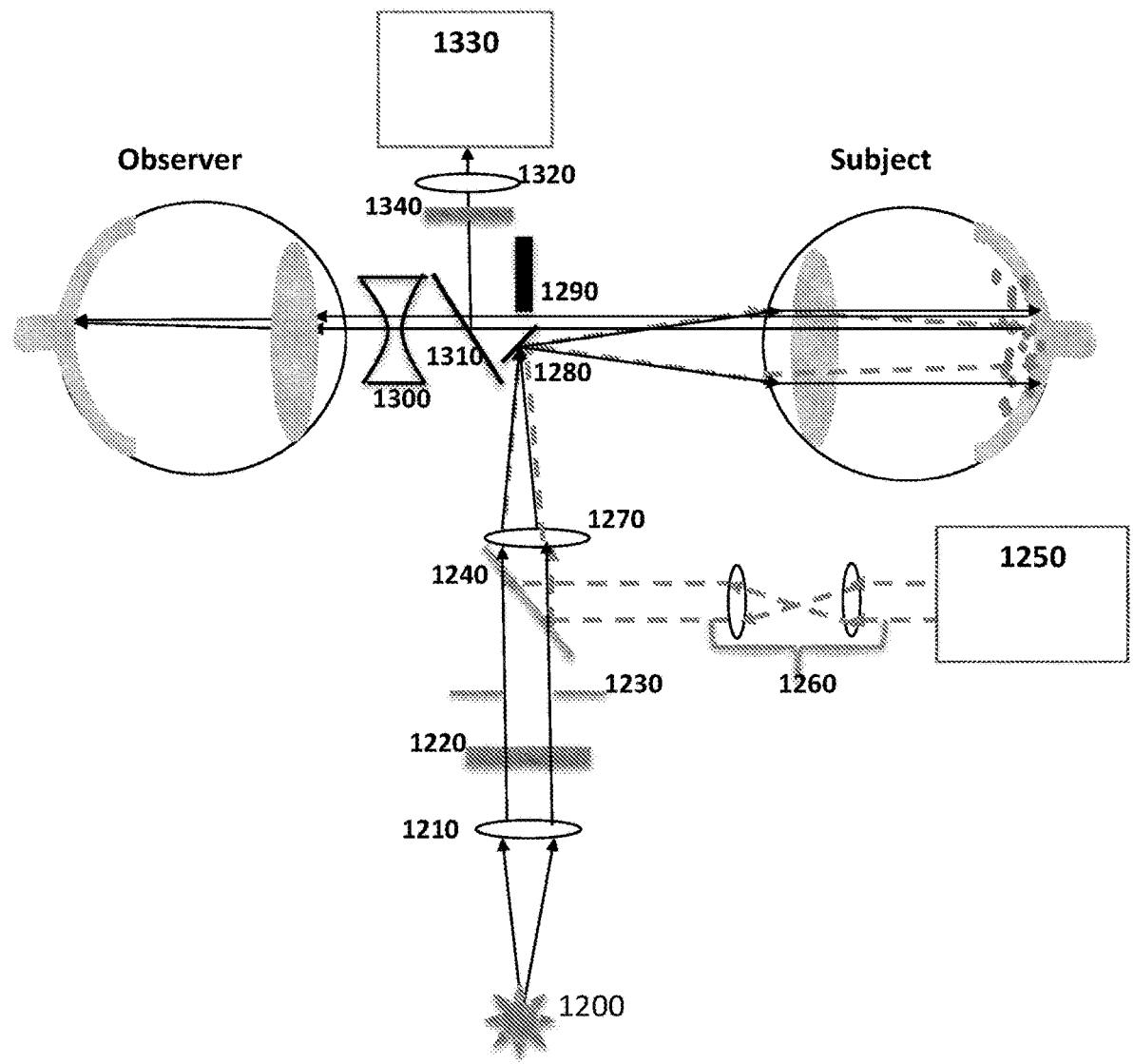

FIG. 12 shows the Schematic of the integrated device for NOD and imaging ophthalmoscope for fluorescence and/or normal fundoscopy. 1200: Visible Light source (LED/lamp/laser); 1210: Lens-1; 1220: excitation band pass filter; 1230: aperture; 1240: Dichroic mirror; 1250 NIR laser and controller; 1260: Beam divergence and expansion controller; 1270: Lens-2; 1280: mirror-1; 1290: hole; 1300: compensation lens; 1310: mirror-2; 1320: Lens-3; 1330: Camera and display; 1340: emission band pass filter.

Figure 13:
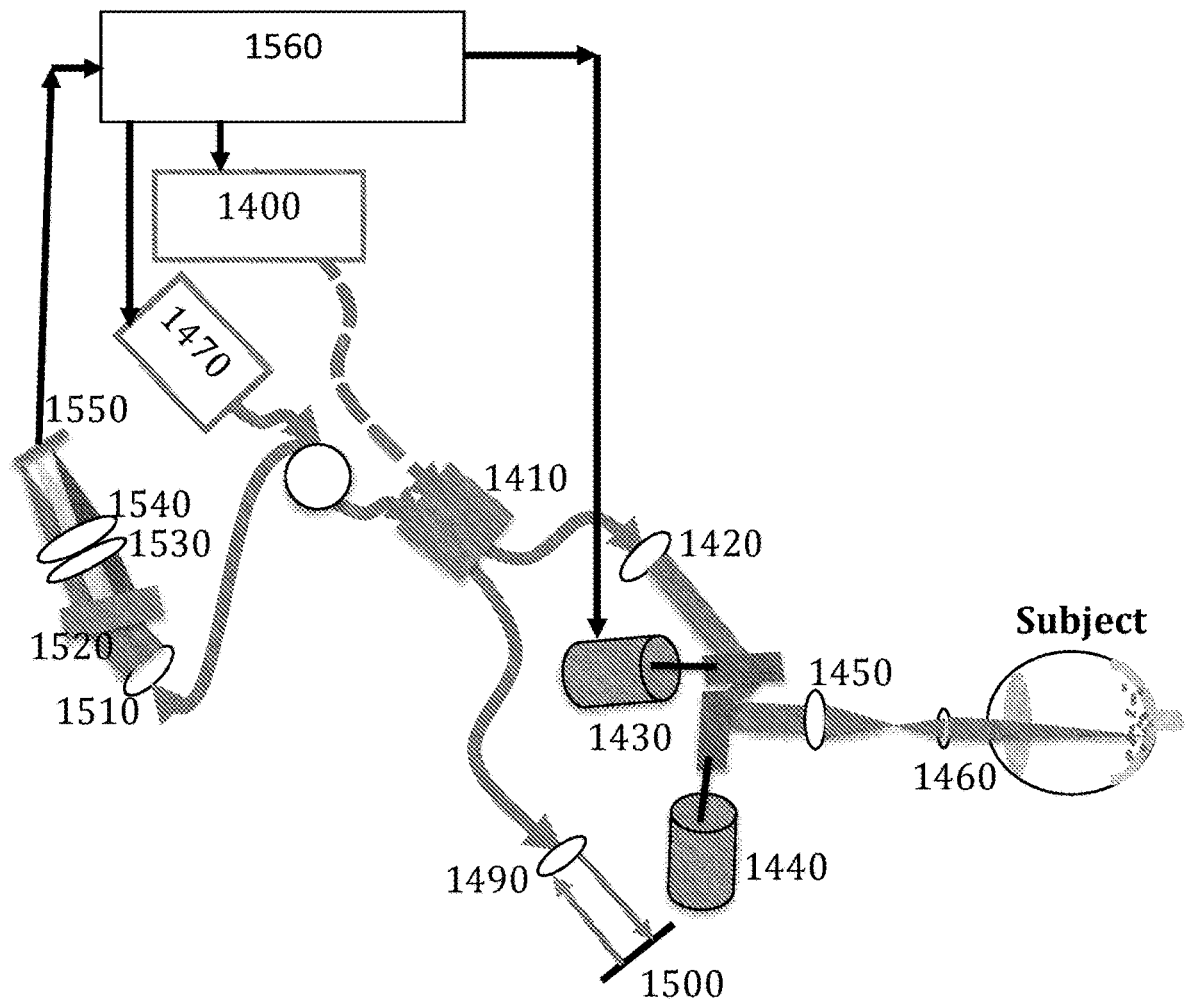

FIG. 13 shows the Schematic of integrated device for NOD and imaging by OCT. 1400: NIR laser; 1410: Fiber coupler; 1420: collimating lens-1; 1430, 1440: scanning mirrors; 1450, 1460: Lens pair; 1470: low coherence source; 1480: Circulator; 1490: collimating lens-2; 1500: reference mirror; 1510: collimating lens-3; 1520: grating; 1530, 1540: lens pair; 1550: camera; 1560: Computer, display and controller.

Figure 14:
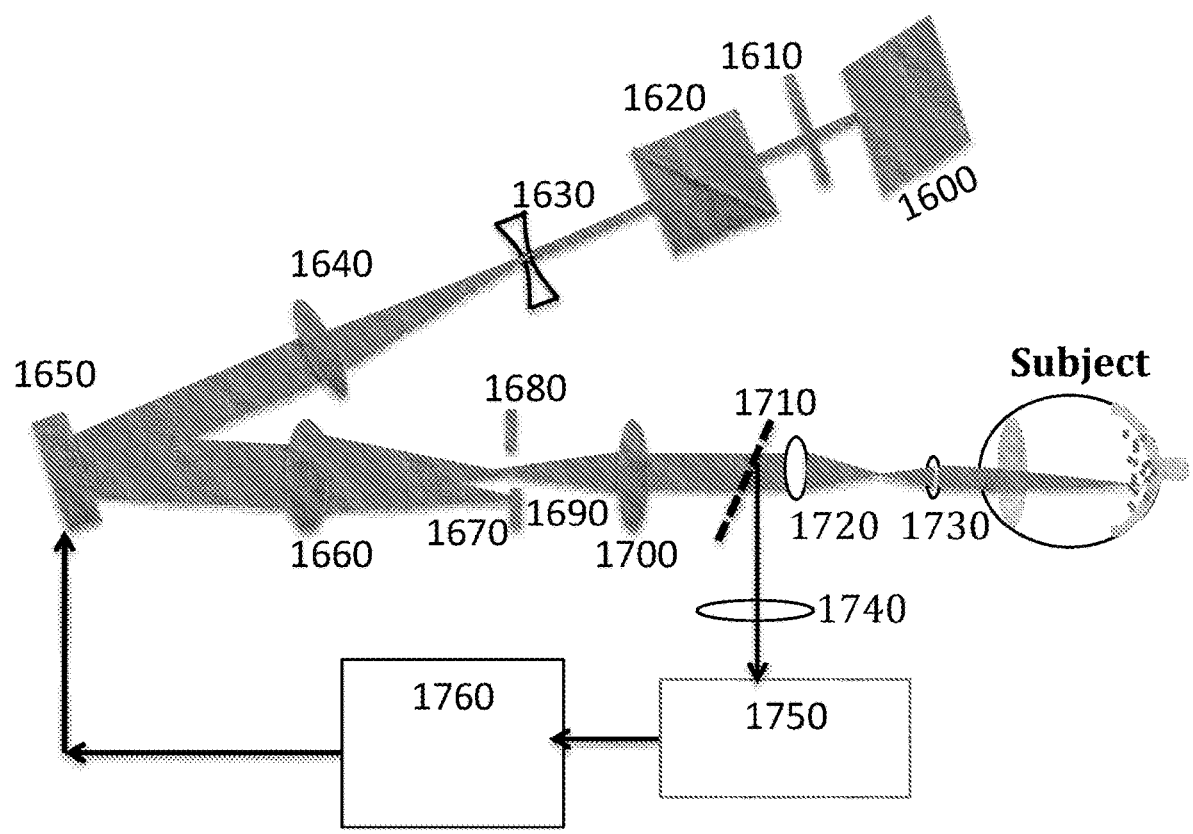

FIG. 14 shows the schematic setup for shaping laser beam for NOD by DMD/SLM to geographic atrophies with feedback imaging by OCT/Fundoscopy. 1600: NIR laser; 1610: half wave plate; 1620: polarizer; 1630: lens-1; 1640: lens-2; 1650: spatial light modulator or Digital micro-mirror device; 1660: lens-3; 1670: un-deviated beam; 1680: pin hole; 1690: modulated beam; 1700: lens-4; 1710: dichroic mirror; 1720: Lens-5; 1730: Lens-6; 1740: Lens-7; 1750: OCT or fundoscope; 1760: Computer and display.

Figure 15:
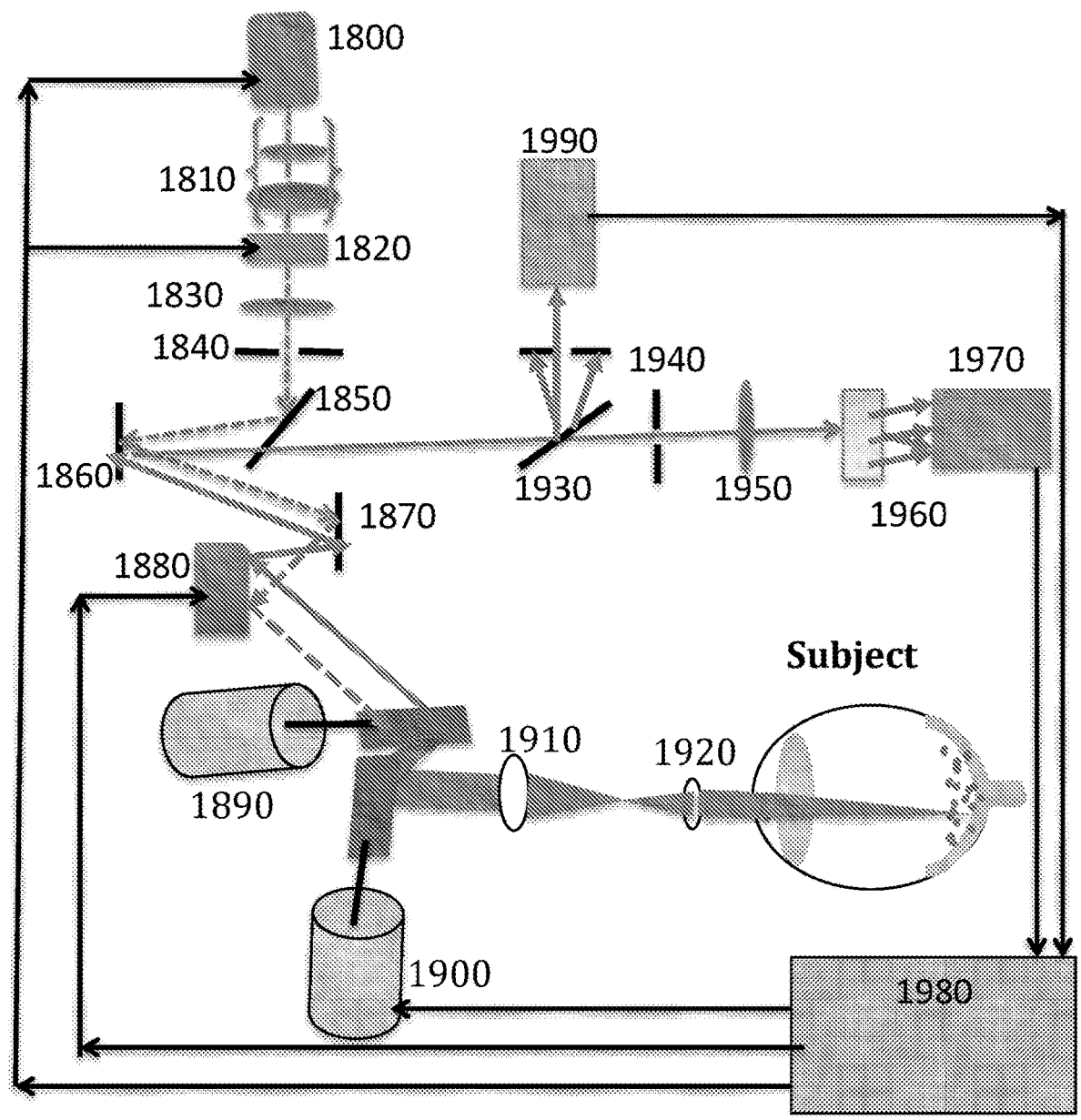

FIG. 15 shows the schematic of adaptive optics setup for correcting laser beam for NOD to geographic atrophy areas of retina. 1800: NOD/imaging laser; 1810: beam expander/collimator; 1820: beam controller (polarization/power/exposure); 1830: lens-1; 1840: pin hole 1; 1850: dichroic mirror; 1860: mirror-1; 1870: mirror-2; 1880: Adaptive optics mirror; 1890: scanning mirror-1; 1900: scanning mirror-2; 1910: lens-2; 1920: lens-3; 1930: beam splitter; 1940: pin hole 2; 1950: lens-4; 1960: wave front sensor; 1970: camera; 1980: computer and controller; 1990: photodetector.

DETAILED DESCRIPTION OF THE INVENTION

The primary method of gene delivery employs viral transfection which has high transduction efficiency. However, use of viruses can lead to unexpected inflammatory responses, immunological reactions, improper gene integration and limit the size of plasmids that can be packaged and delivered (6, 29). Further, viral methods cannot be applied to the delivery of proteins, impermeable drugs, or small molecules, which are required for vaccination and treatment of cancer. Therefore, there have been significant efforts in developing alternative, non-viral methods such as physical (microinjection (30), electroporation (31, 32), ultrasound (33) etc.) and chemically-mediated (e.g. liposomes (34), and biodegradable polymer (35)) methods. These methods suffer from one or more drawbacks, such as invasiveness, reduced efficiency, lack of spatially-targeted delivery and/or having several deleterious effects on transfected cells (31). For example, physical energy required for in-vivo delivery into large animals during electroporation can cause physical and functional damage to the tissue. Most importantly, it is difficult to spatially control the region of gene expression using in-vivo electroporation, virus vectors or chemically mediated methods. This necessitates development of non-invasive method for gene delivery to spatially targeted region(s).

By use of a tightly focused pulsed laser beam, the membranes of targeted cells can be transiently perforated in a minimally invasive manner, allowing exogenous molecules to enter the cell. Over the last decades, laser-assisted perforation has been applied to inject macromolecular substances into single plant and animal cells in a non-contact and non-invasive manner. Initially, lasers in UV (36) and visible were employed for optoporation. However, UV-Visible light has increased potential of damage to organelles as well as to the foreign molecules (such as DNA and proteins) being transferred into the cells. Recently, lasers in the near infrared region (NIR, 700-1000 nm), have received increasing attention because of significantly lower optical loss due to absorption and scattering by cellular component in this range. However, high peak intensity of ultrafast laser beam is required to microinject exogenous materials (46). Though these pulsed lasers are suitable for single cell in-vitro microinjection, difficulties arise for in-vivo delivery of molecules into 3D tissues due to several reasons: (i) The efficiency and throughput for in-vivo delivery is low as it requires high peak intensity of laser beam which needs to be scanned to deliver molecules into a region of interest; (ii) The laser beam's focus and pulse is distorted during propagation inside tissue, thus losing the required intensity to cause in-depth perforation (increasing the laser energy further will cause severe damage to non-targeted cells and tissues before reaching the targeted tissues); (iii) The inherent difficulty in clinical implementation. The instruments' bulk and complexity represent serious operational difficulties. Therefore application of fs laser based delivery has been mostly limited to in-vitro and monolayer cell-culture.

Current methods of delivering agents to the interior of target cells relies on isolation of the cells of interest and inserting the agent into the cell by methods including electroporation, transfection or other harsh methods. To deliver an agent to the interior of a target cell in vivo is even more complicated and relies on identification of a cellular target that is specific for the cell and one that internalizes appropriately for delivery of the agent.

In retinal photodegenerative diseases such as dry age-related macular degeneration (dry-AMD) and Retinitis Pigmentosa (RP), the photoreceptors (e.g., rods and cones) that are responsible for conversion of light into electro-chemical signals, are degenerated. This prevents the generation of photo-induced signals in retina. Loss of photoreceptor cells and/or loss of photoreceptor cell function are the primary causes of reduced light sensitivity and blindness.

Clinical translation of current optogenetic approach for treatment of blindness suffers from lack of method to deliver opsin-encoding genes into spatially targeted regions of degenerated-retina (macula in dry-AMD) without perturbing the non-degenerated retinal regions. Therefore, there is a need for development and optimization of new and efficient non-viral method that can deliver opsin constructs to spatially targeted regions of retina in a minimally invasive manner.

As described herein the introduction of foreign DNA (1), short-interfering RNA (2), small molecules, proteins (3) and drugs into living cells, organs and whole organisms is essential for a variety of applications in genetics, cell and developmental biology, vaccination (4), gene therapy (5, 6) and other therapeutic strategies.

Further, to visualize and control cellular processes, expression pattern and activity, it is necessary to deliver genes encoding fluorescent molecules (proteins for labeling), ion-channels (for activation by light), genetically encoded voltage indicators (GEVI, for detecting activity) and other molecules such as antibodies targeted to membrane and intra-cellular organelles. The primary method of gene delivery employs viral transfection (26-28), which has high transduction efficiency. However, use of viruses may lead to unexpected inflammatory responses, immunological reactions (6, 29) and improper gene integration (29, 61). Further, the viral methods limit the size of plasmid that can be packaged for delivery and also viral methods cannot deliver proteins and antibodies. Further, for understanding of the cellular circuitry, it will be useful to localize the expression of the targeted molecules not only in specific cell types, but to specific cells in restricted spatial regions. Therefore, there have been significant efforts in developing alternative, non-viral methods such as physical (microinjection (30), electroporation (31, 32), ultrasound (33) etc.) and chemically-mediated (e.g. liposomes (34), and biodegradable polymer (35)) methods. These methods suffer from one or more drawbacks, such as invasiveness, reduced efficiency, lack of spatially-targeted delivery and/or having several deleterious effects on transfected cells (31). Most importantly, it is difficult to spatially control the region of gene expression using in-vivo electroporation, virus vectors or chemically mediated methods. This necessitates development of non-invasive method for gene delivery to targeted cells of tissue.

While current methods of delivering agents of choice to particular cell types are somewhat effective, they rely on harsh conditions and the identification of appropriate targeting agents. Moreover, current methods lack specificity, reliability and are largely ineffective in vivo. Accordingly, the present disclosure provides methods and systems for delivering agents to specific cell types and in some embodiments to the interior of specific cell types.

By use of a tightly focused pulsed laser beam, the membranes of targeted cells can be transiently perforated in a minimally invasive manner, allowing exogenous molecules to enter the cell. Over the last decades, laser-assisted perforation has been applied to inject macromolecular substances into single plant and animal cells in a non-contact and non-invasive manner. Initially, lasers in UV (36) and visible (37, 38) were employed for optoporation. However, UV-Visible light has increased potential of damage to organelles as well as to the foreign molecules (such as DNA and proteins) being transferred into the cells. Recently, lasers in the near infrared region (NIR, 700-1000 nm), have received increasing attention because of significantly lower optical loss due to absorption and scattering by cellular component in this range (39-42). However, high peak intensity of ultrafast (39, 42-45) laser beam is required to microinject exogenous materials (46). Though these pulsed lasers are suitable for single cell in-vitro microinjection, difficulties arise for in-vivo delivery of molecules into 3D tissues due to several reasons: (i) The efficiency and throughput for in-vivo delivery is low as it requires high peak intensity of laser beam which needs to be scanned to deliver molecules into a region of interest; (ii) The laser beam's focus and pulse is distorted during propagation inside tissue, thus losing the required intensity to cause in-depth perforation (increasing the laser energy further will cause severe damage to non-targeted cells and tissues before reaching the targeted tissues); (iii) The inherent difficulty in clinical implementation. The instruments' bulk and complexity represent serious operational difficulties. Therefore application of fs laser based delivery has been mostly limited to in-vitro and monolayer cell-culture.

In order to mitigate the challenges in spatially targeted delivery of impermeable molecules to cells and tissues, the present disclosure provides a nano-enhanced optical delivery (NOD) method to achieve targeted delivery into cells in-vitro as well as in-vivo. By nano-enhanced optical delivery (NOD) method is meant use of nanoparticles or nanostructures such as nano-rods, nano-ellipsoids, nano-prisms, nano-stars, nano-shells made out of metal such as gold, silver etc., semiconductors or insulators that can enhance local optical field. The enhancement of the optical (NIR) field is achieved by use of surface plasmon resonance (SPR) of gold nano-rods (GNR) at the tips. This allows use of lower laser power to achieve delivery of impermeable molecules cells, bound to the GNR(s).

By "nanoparticles" as used herein is meant nanoparticles or nanostructures such as nano-rods, nano-ellipsoids, nano-prisms, nano-stars, nano-shells made out of metal such as gold, silver etc., semiconductors or insulators that can enhance local optical field In one embodiment nanoparticles that find use in the methods disclosed herein include but are not limited to gold nano-rods and NIR laser beam of power varying from 10 to 100 mW focused to spots of size ranging from ~0.01 to 1 mm.

In one embodiment a first nanoparticle is functionalized with a first targeting agent using methods known in the art. By targeting agent is meant an agent that binds specifically with a target cell. Targeting agents can be ligands, antibodies, antibody fragments, nucleic acids, aptamers, small molecules and like, so long as the targeting agent is able to bind specifically to one cell type relative to a second cell type. In this way, once the nanoparticle-targeting agent complex is added to a mixture of cells, only the first cell type will be associated with the nanoparticle.

In some embodiments a nanoparticle is functionalized with a second targeting agent specific for a second cell type. In some embodiments nanoparticles are functionalized in 3, 4, 5, 10, 20, 50, 75, 100 or more distinct groups with 3, 4, 5, 10, 20, 50, 75, 100 or more targeting agents to target 3, 4, 5, 10, 20, 50, 75, 100 or more cell types, respectively.

The functionalized nanoparticles are then contacted with a cell type of interest or a plurality of cell types. Notably, however, the nanoparticles only bind to the cell type that is specific for the respective targeting agent. Accordingly, cell can be treated in vitro, ex vivo or in vivo.

In some embodiments nanoparticles having different shapes and therefore SPRs can be used. Nanoparticles having first and second shapes and SPRs can be functionalized with first and second targeting agents to target different cells or can be used to deliver first and second agents to first and second cell types. The aspect ratio (ratio of size of short axis to long axis) of gold nanoparticles can vary from 1:1 to 1:5 to result in SPR peak varying from visible (~530 nm) to NIR (~1100 nm).

Agents to be administered to the interior of the respective cell can be added to a population or mixture of cells. The cells are then irradiated with a laser beam having wavelength matching the peak of the surface plasmon resonance (SPR) of the nanoparticle. It is thought that because the nanoparticle is in close proximity to the cell surface, as a result of the targeting agent, that the SPR causes slight disruption of the cell such that the agent can be delivered to the interior of the cell without killing the cell. In some embodiments, a second nanoparticle-targeting agent complex is contacted with the cell mixture and a second agent is administered to the interior of a second population of cells by repeating the procedure.

Irradiation proceeds at ~10 to 200 mW (focused to a spot size of ~0.01 to ~1 mm) and may last from 1 sec to ~2 minutes. Once irradiation of the sample is complete the samples may be allowed to incubate with the agent for varying periods of time such as from 0.5 sec to 5 hours, or from 1 second to 2 hours or from 2 seconds to 1 hour or from 5 seconds to 30 minutes or from 10 seconds to 10 minutes to around 30 seconds to 5 minutes. In some embodiments incubation proceeds for around 0.5 seconds, around 1 second, around 5 seconds, around 10 seconds, around 30 seconds, around 60 seconds, around 2 minutes, around 5 minutes, around 10 minutes, around 20 minutes, around 30 minutes, around 60 minutes, around 2 hours, around 5 hours, around 7 hours, around 10 hours or around 24 hours.

This disclosure demonstrates that cell-impermeable substances, such as but not limited to plasmids and the like can be introduced into cells in a minimally invasive manner by nano-enhanced optical delivery (NOD) which can include, but is not necessarily limited to nano-enhanced photothermal or photochemical or dielectric breakdown of the membrane leading to local change in membrane permeability. In one embodiment NOD encompasses nano-enhanced photothermal methods using a continuous wave (cw) NIR laser beam. In this Nano-enhanced Optical Delivery (NOD) method, the near-infrared (NIR) field enhancement by gold nano-rods (GNR) is utilized to transiently perforate cell membrane to deliver exogenous molecules to cells via hot spots at the end of the rods. Spatially targeted in-situ delivery is achieved by shining the continuous wave (cw) NIR laser beam in targeted areas.

Agents that can be administered to the interior of a cell according the methods described herein include, but are not limited to cell impermeable agents such as nucleic acids, small molecules, proteins, peptides, antibodies, antibody fragments, particular types of nucleic acids including genes, siRNA, ribozymes, mRNA, modified nucleic acids and modified nucleotides, labels, ions, extra-cellular fluids, vaccines, growth factors, hormones and aptamers.

In one embodiment a cell permeable agent to be delivered is reversibly attached to the nanoparticle. In this embodiment, upon irradiation of the nanoparticle and reversal of the binding of the agent to the nanoparticle, the agent is delivered to the interior of the cell. Delivery to any cell type can be accomplished by the methods disclosed herein.

According to the methods described herein, NOD of impermeable molecules (e.g. genes) into the skin was achieved using a near-infrared laser beam.

In one embodiment the disclosure provides methods of treating diseases by administering a therapeutic agent to a cell or cells of interest. In one exemplary embodiment, the disclosed invention provides method for the use of NOD method to deliver opsins for vision restoration applications in patients with retinal photodegenerative diseases such as RP and dry-AMD. Most of the current clinical treatments are primarily focused on slowing down the progression of the disease (62), as there is neither a cure that can stop the degeneration (63) nor a therapy, other than retinal prostheses, that can restore vision lost due to the degeneration (64). Since higher order neurons are still intact in photodegenerated retina, several stimulation methods target the higher order neurons, e.g. Bipolar cells and retinal Ganglion cells, which carry the visual information to the visual cortex. While direct electrical stimulation approaches require mechanical contact of electrodes to the retinal cells, indirect stimulation approaches such as optogenetic stimulation does not necessitate such physical contact. Optogenetic stimulation involves delivery of plasmids encoding light-activatable ion-channels to cells. Once expressed on cell membrane, irradiation with suitable light wavelength activates the ion-channels (enhancing inward/outward flow of anions or cations) and thus, cell(s) get depolarized or hyperpolarized. Thus, the indirect methods provide clear advantage of being non-intrusive. In addition, cellular specificity and high (single cell) resolution can be achieved while using optogenetic stimulation.

Currently, use of optogenetic sensitization of retinal cells combined with activation/inhibition has allowed the possibility of replacing the retinal implants, eliminating the requirement of placing electrodes near every single neuron for high resolution (65). Optogenetic stimulation provides high temporal precision (9, 10, 12, 13, 66, 67) by introducing light-activatable molecular channels (opsins) into cells by genetic targeting. In addition to higher temporal and spatial resolution, optogenetics has several advantages over electrical stimulation such as cellular specificity (e.g. spared cones, ganglion or bipolar cells) and minimal invasiveness (68). Light-induced activation of ChR2, a non-selective cation channel, results in depolarization of only those cells that express ChR2. Selective activation of neurons by ms-pulsed blue light has been demonstrated in culture (67), brain slices, as well as in small animals (69-72). This optogenetic activation method is very promising for controlling cellular activities in-vitro as well as in-vivo as it only requires light of moderate intensity (<0.1 mW/mm$^2$) that can be delivered from a light emitting diode (LED) or laser (9, 10). Various light-activated ion channels (opsins) have been developed to either enhance photosensitivity of cells, or to be activated by different wavelengths of visible light.

Optogenetic methods have been employed for vision restoration in blind mice model either by non-specific stimulation of retina (73) or in a promoter-specific manner including Thy1 for RGCs (74-78), mGluR6 targeting ON bipolar cells (24, 79). Attempts have also been made for stimulation of RGCs by use of melanopsin (80) or photochemical genetics (81). Further, use of active light stimulation of chloride-channel opsin (Halorhodopsin) expressing in longer-persisting cone photoreceptors (82) has shown new promise for therapeutic intervention for restoration of vision (83). The re-sensitized photoreceptors have shown to drive retinal circuitry functions, activate cortical circuits, and mediate visually guided behaviors.

Vision restoration by optogenetics or other gene therapy methods has been proposed in humans by delivery of opsin or other genes via viral means (e.g. recombinant adeno-associated virus, or lenti virus) in to the vitreous of the eye. However, clinical translation of such therapy (using optogenetic activation) for vision restoration is limited to a small population of patients (having complete photodegeneration over the whole retina) by the lack of approach for delivery of MCO-encoding genes into spatially targeted regions of degenerated-retina (i.e. macula in dry-AMD). Therefore, there is a need for deployment of new and efficient non-viral method that can deliver large constructs to spatially targeted regions of retina in a minimally invasive manner.

The efficient localized photothermal conversion by gold nanostructures (52-60) in the safe NIR spectrum allowed in vivo nano-enhanced optical delivery (NOD) of opsin-plasmids into cells in targeted regions of photodegenerated retina in animal models using external NIR laser beam (800 nm) power varying from 50 to 200 mW with exposure of 5 to 15 sec. Gold nanoparticles found to have negligible cytotoxicity, making it suitable for clinical NOD. That is, in this exemplary embodiment GNPs are used to deliver plasmids encoding opsin into the retina of subjects in need thereof. As appreciated by one of ordinary skill in the art diverse diseases can be treated by the methods described herein. Methods of treating such diseases include in vitro, ex vivo or in vivo administration of otherwise cell impermeable agents to the cells.

The method can be used for both gene augmentation therapy and gene inhibition therapy without triggering immune response unlike viral vectors. Non-limiting examples of ocular disorders that find use of the methods and systems described herein include photodegenerative diseases of eye including RP, AMD, Stargardt's, LCA, cone-rod dystrophies, Usher syndrome. Non-limiting examples of other disorders that find use of the methods and systems described herein include muscular dystrophy (Duchenne and Becker), cystic fibrosis (in which the lungs and digestive system become clogged with thick, sticky mucus), and children with severe combined immunodeficiency.

The NOD method will assist in delivery of CRISPR-Cas9 therapeutic molecules to cells (e.g. T-cells) both ex-vivo and in-vivo for treatment of many disorders including cancer. In some embodiments ex vivo gene transfer finds using the methods disclosed herein. Transformation of bacteria with delivery of exogenous genes using NOD is useful. Delivery of genes and other therapeutic molecules to ovum, embryos, sperms used in in-vitro-fertilization will be useful in reproductive medicine. Further, NOD method can be used for delivery of genes and other small molecules for use in developing genetically modifies plants. Further ex-vivo use include delivery of molecules using NOD to genetically modify chimeric antigen receptor T cells for cancers including advanced acute lymphoblastic leukemia. The NOD method will assist in delivery of molecules (Plasmids, RNAs, proteins etc.) to cells for reprogramming during stem cell production for enhancing treatment of many disorders upon implantation of these stem cells.

The disclosure also provides design of several devices for targeted delivery including scanning of the beam, shaping the beam, and achieving wave front-correction. In addition, the invention in some aspects provides integrated nano-enhanced optical delivery (NOD) device with fundoscopy, scanning laser ophthalmoscopy, and Optical coherence tomography to identify targeted region requiring delivery of therapeutic molecules.

The invention in some aspects includes expression of Opsins in cells in-vitro or in-vivo as well as methods for modulating cellular activities by these opsins. The results presented in this invention show efficient and stable in-vivo expression of opsin-reporter protein in mice retina after intravitreal injection of opsin with NOD agent (GNRs).

According to yet another aspect of the invention, method of restoration of vision in human is provided. The method includes use of NOD to deliver opsin-genes to targeted areas of retina, and/or in combination with different imaging modalities to provide feedback to the NOD-beam scanning/shaping devices. The opsin-expressing cells produce photo-induced inward current similar to photoreceptor cells, thus enabling vision restoration.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a molecule or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

Below, the presently disclosed invention will be further described by way of examples, which are provided for illustrative purposes only and accordingly are not to be construed as limiting the scope of the invention.

EXAMPLES

Example 1

Figure 1:
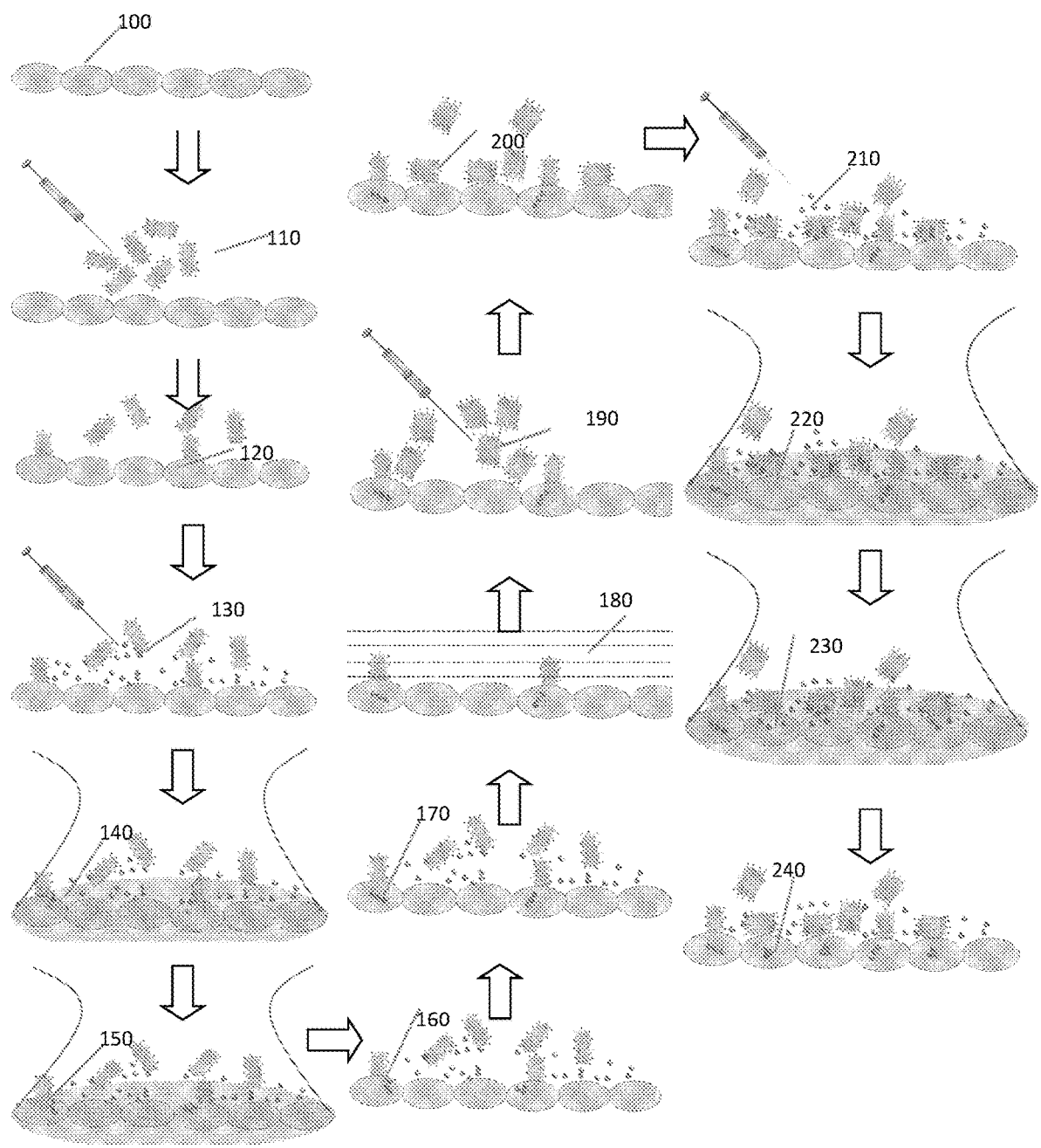
FIG. 1 depicts various steps of the Nano-enhanced Optical delivery to specific groups of cells in-vitro or in a tissue in-vivo.

FIG. 1 illustrates various steps of the Nano-enhanced Optical delivery to specific groups of cells in-vitro or in a tissue in-vivo.

Step 1: Gold nano-rods, functionalized to bind specific cells, are added to extracellular medium.

Step 2: The functionalized gold nano-rods are allowed certain incubation period to bind to the targeted cells.

Step 3: The to-be-delivered molecules such as plasmids or antibodies are added into the extra-cellular medium.

Step 4: The near-infrared (NIR) laser beam wavelength is tuned to Surface Plasmon Resonance peak (SPR) of the gold nano-rods (GNR). The sample or the beam is either scanned (by scanning mirrors or stages) or spatially modulated (for example by spatial light modulator or digital micro-mirror device) to cover the targeted area. The NIR laser irradiation of the GNRs creates hot spots at the end of the rods and if bound to cell membrane, increases local membrane permeability.

Step 5: Thus, the otherwise-impermeable molecules enter via membrane exposed to hotspots. The delivery of exogenous molecule to the cells is dependent on the total exposure and power of the NIR laser beam. Further, delivery efficiency depends on the concentration of the GNRs, their binding with cells, match of the SPR peak of the GNRs with the NIR laser beam, all of which can be determined by one of skill in the art. While continuous exposure to NIR laser beam can be used to accomplish such nano-enhanced optical delivery, the laser may be pulsed (width varying from several picoseconds to minutes) in order to optimize delivery without overall heating of the cells/tissues.

Step 6: After switching off the laser beam, certain time period (seconds to minutes or even several hours) may be allowed for the exogenous molecules to enter the cells and bind to targeted organelles, and activate or be activated by cellular machineries such as gene expression. Then the unbound rods and to-be-delivered molecules can be washed in case of in-vitro NOD. In case of in-vivo, the excretory system of the organ will accomplish this.

Step 7: To deliver same of different molecules to another cell types, gold nano-rods of different shape (i.e., different SPR peak) are functionalized with different moieties to bind to new type of cells.

Step 8: The functionalized GNRs are added to the extracellular medium and allowed incubation period to bind to the next group of targeted cells.

Step 9: The new to-be-delivered molecules are added into the medium. The concentration of added molecules (in addition to concentration of differently shaped GNRs) are varied for obtaining different intra-cellular delivery.

Step 10: The near-infrared (NIR) laser is tuned to surface Plasmon resonance (SPR) peak of the newly added gold nano-rods (GNRs). The targeted areas of cells/tissue is(are) irradiated with the new SPR-matched NIR laser beam.

Step 11: The new molecules enter into next group of GNR-bound cells via hotspots created during the laser irradiation and thereafter until the cell membrane permeability is perturbed.

Step 12: The injected new molecules are allowed to bind with targeted organelles in $2^{nd}$ group of cells. In case of genes or other small molecules, the cellular machineries act either to express the gene or suppress desired activity.

Example 2

For spatially targeted delivery of different molecules to different types of cells, gold nano-rods with different shapes (long to short axis aspect ratios) were created. FIG. 2A shows high magnification electron microscopic image of gold nano-rods used for optical enhancement of laser beam (hot spots) at the ends of the rods. These nano-rods were functionalized with PEG, Concanavalin A or Antibodies for target-specific binding to different types of cells. Varying shape of these gold nano-rods allowed wavelength-selective Surface Plasmon enhancement. FIG. 2B shows the measured optical density of type1 gold nano-rods showing SPR peak at 800 nm. The optical density of type 2 gold nano-rods having peak at 850 nm is shown in FIG. 2C. To evaluate wavelength-selective delivery, cells were attached with functionalized gold nano rods of type 1 (SPR peak 800 nm) and irradiated with SPR-mismatched 850 nm laser beam. Propidium iodide (cell-impermeable molecule) was added to the extracellular medium. No intracellular delivery was observed in case of SPR-mismatched laser irradiation. However, with irradiation at 800 nm with same laser power and exposure lead to distinct delivery into spatially targeted cells (bound with type 1 GNRs). Thus, tuning the NIR laser wavelength allowed selective delivery to targeted population of cells.

Example 3

To investigate nano-enhanced optical delivery into cells, a prototype was developed where multiple NIR lasers were coupled to a microscopic platform. FIG. 3A shows the schematic of a set up for nano-enhanced optical delivery into cells. The CW Laser (400) beam (800 or 850 nm) was expanded and collimated using a combination of Focusing Lenses (410) and coupled to the microscope using a dichroic mirror 1 (440). The Condenser Lens (420) focused the NIR beam on to the sample. Vertical translation of the condenser lens led to control of the irradiation spot size in the Sample chamber (450). For multiple or patterned delivery of molecules the XY stage (460) was translated. The imaging white light (430) is transmitted via the dichroic mirror 1(440). The Microscope Objective (470) collected the transmitted white light through the sample. For Fluorescence excitation of the sample a Fluorescence excitation lamp (490) was used. The choice of excitation band pass filter (500) was made based on the characteristic fluorescence of the molecule under investigation. The Dichroic mirror 2 (480) reflected the excitation light on to the sample via the microscope objective. The emission Filter (510) transmitted the characteristic fluorescence emission from the molecules under investigation. The Laser cut-off filter (520) blocked the NIR laser beam from reaching the Camera (530). The actual Picture of the laser coupled upright fluorescence microscope for nano-enhanced optical delivery into cells is shown in FIG. 3B. While this set up is utilized for demonstrating the mechanism of NOD, by no means it may be construed as the only way the proposed method can be realized. Other means include use of inverted microscope, single fiber or fiber optic probe, scanning of the beam or shaping the beam using spatial light modulator or digital micro-mirror device.

Example 4

FIG. 4, demonstrates use of gold nano-spheres and green laser beam (532 nm) for delivery of exogenous impermeable molecules. Bright field and fluorescence images of HEK cells before green laser beam irradiation is shown in FIG. 4A and FIG. 4B respectively. FIG. 4C shows green laser beam spatially-targeted to cell(s) in the sample chamber. Increase in fluorescence indicating influx of exogenous molecule (Propidium Iodide, PI) is evident in FIG. 4D and FIG. 4E. FIG. 4F shows Bright field image after XY-movement of sample stage to allow delivery into different cells/region. FIG. 4G shows Epifluorescence image after sample repositioning. The near infrared cw laser irradiation is again carried out as shown in panel FIG. 4H. FIG. 4I and FIG. 4J show rise in fluorescence indicating influx of exogenous molecule (PI) in new targeted cell(s). Besides low penetration depth of green light in biological tissue, severe concerns (cell damage) remain on use of green laser in tissues in-vivo for NOD requiring near-infrared based approach.

Example 5

FIG. 5 shows use of gold nano-rods and NIR laser beam (800 nm) for delivery of exogenous impermeable molecules into HEK cells. Gold nano-rods (diameter: 10 nm, length: 40 nm) with surface Plasmon absorption maximum at 800 nm were used for NOD. FIG. 5A shows bright field image of cells attached to functionalized gold nano-rods. For membrane specific binding, these nano-rods were functionalized with Concanavalin A (Con A) molecule, which has been shown to exclusively bind to membrane of the cells. In our initial in-vitro NOD experiments, Propidium iodide (PI)—the impermeable DNA binding molecule was delivered into the HEK cells to optimize the NOD method. Different laser power (20, 50, 100 mW) and exposures (1, 2, 5, 10, 20, 30, 60, 90, 120 sec) were used to optimize the NOD process. The enhanced photothermal properties of the NIR-absorbing nanoparticles on cell membranes enabled localized temperature rise allowing delivery of impermeable molecules via cell membrane during cw NIR laser ON condition. For optimal laser dose, the viability of cell remained intact as confirmed by Calcein-exclusion assay. The influx of exogenous molecules stopped upon switching-off the laser beam, while cell morphology remained intact.

Then, NOD was used to deliver impermeable actin-staining molecules (Alexa 488 Phalloidin). The Fluorescence image of Alexa 488 Phalloidin incubated in extracellular medium before NOD is shown in FIG. 5B. The enhanced optical properties of the NIR-absorbing gold nano-rods (GNR) on cell membranes resulted in localized temperature increase (at hot spots) upon continuous wave (CW) laser irradiation allowing the delivery of impermeable molecules via cell membrane. Increase in Alexa 488 Phalloidin fluorescence intensity and cellular distribution observed after wide-area irradiation by cw NIR laser beam (800 nm) are shown in FIG. 5C, FIG. 5D, and FIG. 5E.

To date all antibody-based therapy has been extra-cellular based and not spatially targeted. Delivery of antibodies to live cells in targeted regions of tissue is important to visualize structure and functioning of cells as well as for therapeutics. Antibody delivery to intra-cellular organelles provides high specificity in binding targeted molecules (on the organelle) in contrast to non-specific binding by dyes. However due to their large size and membrane impermeability, most studies have been limited to fixed cells and thus does not provide necessary temporal resolution to discern changes upon neuronal modulation. Viral methods cannot be applied for delivery of antibodies, staining molecules, proteins, or impermeable drugs. Therefore, there have been significant efforts in developing alternative, non-viral methods such as physical (microinjection (30), electroporation (31, 32), ultrasound (33) etc.) and chemically-mediated (e.g. liposomes (34), and biodegradable polymer (35)) methods. Very few studies have utilized high extracellular potassium to deliver antibodies into cells (84, 85). Though such studies have allowed important studies on synaptic vesicle dynamics (84), high potassium perturbs the physiological environment and activity of cells. Further, it cannot be spatially targeted to selected cells. Thus existing methods suffer from one or more drawbacks, such as invasiveness, reduced efficiency, lack of spatially-targeted delivery and/or having several deleterious effects on micro-injected cells (31).

FIG. 6 shows use of gold nano-rods and NIR laser beam (800 nm) for delivery of exogenous impermeable antibodies labeled with Alexa 488. FIG. 6A shows bright field image of HEK cells attached to functionalized gold nano-rods (SPR peak at 800 nm). The fluorescence image before NOD is shown in FIG. 6B. The increase in intracellular fluorescence intensity (suggesting antibody delivery) observed after wide-area irradiation by cw NIR laser beam (800 nm) is shown in FIG. 6C, FIG. 6D, and FIG. 6E. Use of wavelength-detuned laser beam (850 nm) at same power and exposure did not lead to nano-enhanced optical delivery into the gold nano-rod attached cells.

Example 7

To demonstrate nano-enhanced optical delivery into retinal cells, the mouse retinal explants was used. Adult rd10 deficient mice were sacrificed using $CO_2$. The photodegenerated retina was removed and cut into 1 mm×1 mm square explants using a tissue chopper. The explants were placed onto coverslip previously coated with 5 μg/dish of Poly-D-Lysine. FIG. 7A shows bright filed image of a retinal explant. The retinal explants were incubated with Con A conjugated gold nano-rods for 1 hr at 37° C. The impermeable DNA binding molecule: Propidium iodide was added to the extracellular medium. After 10 minutes of incubation, the explants were viewed under the epifluorescence microscope to quantify the baseline prior to laser exposure (FIG. 7B). NOD was then carried out in a region of diameter 0.5 mm (area: ~0.2 $mm^2$) in each explant. Delivery of PI into retinal cells was monitored using epifluorescence microscope immediately after the laser exposure. Fluorescence images after exposure of near infrared laser (30 sec) in presence of GNR is shown in FIG. 7C. Three laser exposure durations (30, 60, 120 sec) were used. The fluorescence (indicator of delivery) in NOD regions in presence of GNR (FIG. 7C) was quantitatively compared with the condition where laser exposure of retinal explant was carried out without gold nano-rods (FIG. 7D). In the absence of GNR, no detectable increase in fluorescence was observed after 30 sec laser exposures of the retinal explant (FIG. 7D).

Example 8

To establish in-vivo gene delivery using NOD, we used GFP plasmids and nude mice as model. A 5 μl drop of (1:2) mixtures of nanoparticles and GFP plasmids is injected in the skin of nude mouse (marked by arrow in FIG. 8A). Targeted irradiation with cw NIR laser beam (800 nm) for 2 min on the site was carried out for NOD (FIG. 8B). GFP expression in targeted tissue was analyzed 48 hrs. after NOD using an upright fluorescence microscope. GFP expression in NOD region vs. neighboring control region (separated by the dotted white line) is shown in FIG. 8C. Thus, targeted delivery of plasmids into tissues can be realized using cw NIR laser beam based NOD.

Example 9

One of the examples where opsin is used for treatment of disease is blindness caused by retinal photodegenerative diseases. Retinitis Pigmentosa (RP) and dry age-related macular degeneration (dry-AMD) refer to disorders characterized by degeneration of photoreceptors in the eye that hinders visual ability by non-functional neuronal activation and transmission of signals to the visual cortex (86-90). While (dry) AMD is the leading cause of new vision loss in ~15 million persons older than 65 years of age (91), the prevalence of RP is at least one million individuals worldwide (92, 93). RP is most often inherited as an autosomal recessive trait with large number of cases having this form of inheritance (88, 92, 94). Further, the degree of visual loss increases with ageing (95) and this is a major concern for demographic changes towards elderly population.

After the successful in-vitro NOD experimental results in rd10 mice retinal explants, in-vivo transduction of opsin plasmids into the retinal cells of rd10 mice was carried out using the NOD technique. The rd10 mice (retinal degeneration 10, spontaneous missense point mutation in Pde6b) have a later onset and progressive retinal degeneration, closer to the human retinal photodegeneration phenotype. FIG. 9 represents a schematic of the retina showing loss of photoreceptors (Rod, cone) in the encircled region of the retina. Different cellular layers of retina in this targeted photodegenerated region can be microinjected with exogenous therapeutic molecules by NOD-based controlled delivery.

FIG. 10 shows schematic process of NOD-based controlled molecular delivery in targeted regions of retina. The molecules (e.g., genes) injected into the vitreous through sclera. When a near-infrared (NIR) laser irradiates targeted regions of retina (circle), membrane of retinal cells bound with appropriate nano-rod(s) gets permeabilized for exogenous impermeable molecules (e.g. genes). The in-vivo gene delivery system consists of external optics (adaptive/scanning) for correcting beam propagation through cornea and lens in the eye to allow irradiation of spatially targeted regions of retina to be delivered with exogenous molecules. The gene delivery system is integrated with retina imaging modalities including Scanning laser Ophthalmoscopy, Optical Coherence Tomography and Fundoscopy.

Example 10

Nano-enhanced Optical Delivery using NIR laser beam was carried out with the in-vivo setup (FIG. 11A). Gold nano-rods (diameter: 10 nm, length: 40 nm) with surface Plasmon absorption maximum at 800 nm were used for NOD. The rd10 mice (N=6) were anesthetized with a mixture of ketamine (65 mg/kg), xylazine (7.5 mg/kg), and acepromazine (0.5 mg/kg). One drop of local anesthesia (0.5% proparacaine hydrochloride) was instilled into both the eyes of the animals. The functionalized gold nano-rods and 2 μl of opsin-mCherry plasmids (final concentration: 50 ng/μl) was injected into one of the eyes by a sterilized 32-G needle of a Hamilton micro-syringe inserted through the sclera into the vitreous cavity. As a negative control, the other eye was intravitreally injected with same volume of PBS. 1% Tropicamide ophthalmic solution was applied for dilating the pupil. The Pupil dilation can be seen the confocal laser scanning reflectance microscopic image (FIG. 11B). The cornea was kept moist with a balanced salt solution during the entire surgical procedure. The CW NIR laser beam exposure was varied. FIG. 11C shows the zoomed image of eye during the NOD laser exposure of the eye, injected with GNR and opsin plasmids. 5 weeks after injection of AAV-mGluR6-MCO-mCherry, the mice were sacrificed and retinal tissue was extracted. The confocal fluorescence image (FIG. 11D) shows expression of opsin-mCherry in the retinal cells. The retina of PBS-injected control eye does not show any characteristic (mCherry) fluorescence. Further, the peripheral retina (without NIR laser irradiation) served as internal negative control.

While NOD method successfully demonstrated targeted gene delivery into mice retina, successful delivery of therapeutic genes in humans, having thick inner limiting membrane (ILM) (96), may require use of chemical agent (e.g. AAA) that can transiently permeabilize the inner limiting membrane of the human eye.

Example 11

For use of NOD in eye of human subjects, an integrated system comprising of NIR laser for NOD and target retina examination by slit lamp Ophthalmoscope/fundoscopy is presented. FIG. 12 shows a Schematic diagram of the integrated device for NOD and imaging ophthalmoscope for fluorescence and/or normal fundoscopy. Light emitted from 1200 (a visible light source such as LED, lamp or laser) is expanded/collimated/focused using lenses (1210), transmitted through the aperture (1220) and directed to the retina by mirror 1 (1280). The excitation band pass filter (1220) is optionally used for selecting excitation band in case of fluorescence examination of the retina. The near-infrared NOD laser (1250) beam is expanded by a beam divergence and expansion controller (1260) and directed to the subject's eye by use of the dichroic mirror (1240), lens (1270) and mirror 1 (1280). Light reflected (or fluorescence) from the retina is collected by a combination of mirror 2 (1310), lens 3 (1320) and optionally through an emission filter (1340). The compensation lens (1300) is used by the observer to visualize the subject's retina. After identifying the pathological areas, the subject's eye(s) will be injected with GNR and therapeutic molecules. The observer-operator will then target the NIR laser beam to the pathological areas and will expose those areas to clinically/pre-clinically tested doses (i.e., power and exposure time) within safety limit.

Example 12

Further, for use of NOD in eye of human subjects, an integrated system comprising of NIR laser for NOD with device for obtaining feedback by optical coherence tomography (OCT) is presented. FIG. 13 shows a schematic setup of integrated device for NOD (1400) and feedback imaging by OCT. The OCT system consists of a NIR low coherence source (1470) which is routed through a Circulator (1480) into a 2×2 Fiber coupler (1410). The NIR laser (1400) for NOD, selected to have a wavelength spectrally separated from that of the OCT source, is coupled to the second input channel of the fiber coupler (1410). The NOD laser beam emanating from the out put of the fiber coupler is collimated by a collimating lens (1420) and targeted to selected retinal areas by scanning mirrors (1430, 1440) and pair of telescopic lenses (1450, 1460). During identification of retinal pathology, the NIR laser beam for NOD is switched off. The beam from the low-coherence source (for OCT), at the output end of FC is collimated by the same collimating lens (1420) and scanned by the pair of mirrors (1430, 1440). The OCT beam is delivered to the eye by use of telescopic lenses (1450, 1460). The reference beam emanating from the other port of the fiber coupler is collimated by another collimating lens (1490) and reflected back via the same port by use of reference mirror (1500) as shown in FIG. 13. The back-reflected sample beam from the eye (and retina) and the reference beam are routed back via the circulator (1480) to a spectrometer, which comprises of grating (1520) and lenses (1530, 1540). The interferrogram is recorded in a camera (1550) and processed to obtain structural information of the eye and retina in particular, indicating its pathological condition. The regions of interest for NOD will be marked on the image displayed on the viewing screen (1560).

After identifying the pathological areas that need treatment, the subject's eye(s) will be injected with GNR and therapeutic molecules into the vitreous cavity or sub-retinal space depending on the targeted retinal layer. The NIR laser beam will be switched ON and targeted to the pathological region(s) of interest. These areas will be exposed to clinically tested NIR laser doses (i.e., power and exposure time) for efficient and minimally invasive delivery of therapeutic molecules.

During Nano-enhanced optical delivery, the OCT beam is kept turned ON so as to allow imaging of the region(s) of interests that will provide feedback (about the eye movement) to the NOD laser beam delivery process so that the NOD laser beam scan can be dynamically readjusted to match the region(s) of interest. Though NOD integrated with Spectral Domain OCT has been presented here, the invention does not exclude use of other OCT modalities for identifying retinal pathologies and providing feedback to the NOD laser beam delivery.

Example 13

In case of rapid movement of organ (e.g. eye), it may be advantageous to use a spatially sculpted NIR beam to match the shape of the region(s) of interest in the tissue requiring targeted molecular delivery by NOD. FIG. 14 depicts schematic of a setup for shaping the NIR laser beam for NOD by DMD/SLM to fit the targeted regions (e.g., geographic atrophies of retina in photodegenerative diseases) so that the therapeutic molecules (e.g. genes) can be delivered in a high throughput manner. In this method, feedback imaging by OCT or Fundoscopy can be obtained to ensure exact matching of the NOD laser beam to the targeted areas. After identifying the pathological areas, the subject's eye(s) is(are) injected with GNR and therapeutic molecules. For controlling the power and/or polarization of the NIR laser beam (1600) used for NOD, the beam is transmitted through half wave plate (1610) and polarizer (1620). The beam is expanded and collimated by lenses (1630, 1640), which illuminates a spatial light modulator or Digital micro-mirror device (1650). The 1650 is programmed to modulate the laser beam shape (based on feedback by OCT or fundoscopy) so as to match the regions of tissues requiring NOD laser molecular delivery. The un-deviated beam (1670) from the 1650 is blocked by a lens (1660) pinhole (1680) assembly. The spatially modulated beam (1690) is transmitted through the 1680, collimated by a lens (1700) and transmitted through the dichroic mirror (1710) to the telescopic lens pair (1720, 1730) that delivers the beam to the tissue (e.g. retina). The pathological area(s) is (are) exposed to the clinically/pre-clinically tested doses (i.e., power and exposure time) of NIR laser beam within safety limit.

Example 14

In addition to motion artifacts, challenges in perfectly matching the margins of the NIR laser for NOD may arise due to scattering tissue and imperfect optical media of the eye. To correct for wave front distortions in NOD laser beam (1800), use of adaptive optics is presented as shown in FIG. 15. This is to improve the performance of the NOD process. This is accomplished by compensating for the higher order aberrations originating from the cornea and the lens of the eye by using deformable adaptive optic mirror (1880). FIG. 15 shows a schematic of the setup utilizing adaptive optics for correcting the laser beam for nano-enhanced optical delivery of molecules to cells in the geographic atrophy areas of retina. The NOD laser beam (1800) is expanded and collimated by a beam expander (1810). The beam controller (1820) controls the polarization, power and exposure of the NOD laser beam. The beam after passing through lens (1830) and pinhole (1840) is reflected by a dichroic mirror 1 (1850) to folding mirrors (1860, 1870) that directs the beam to the deformable adaptive optic mirror (1880). First the NOD laser beam is operated in low power mode to initialize the 1880. The beam is maneuvered by pair of scanning mirrors (1890, 1900), which sends the beam (dotted arrows) to retina via the telescope lens pair (1910, 1920).

The back-reflected beam from eye with distorted wave front (solid arrows) traverses via the dichroic mirror 1 (1850) to the beam splitter (1930). The reflected part of the beam (from 1930) passes through a pinhole (1940) to a photodetector (1990) to enable ocular imaging (similar to scanning laser ophthalmoscope). The transmitted beam (through 1930) passes through a pinhole and lens (1950) to a wave front sensor (1960) such as Shack-Hartmann's. The wave front distortion mapped in near-real time is used to control the 1880 so as to compensate for the distortions in the NOD laser beam at operational conditions. After identifying the pathological areas, the subject's eye(s) is injected with GNR and therapeutic molecules. Then irradiation of the spatially targeted regions of retina is carried out by wave front corrected NIR laser beam at clinically/pre-clinically tested doses (i.e., power and exposure time) within safety limit.

For optogenetic vision restoration, patient-to-patient variability and time-dependent changes in spatial-distribution of retinal-degeneration demands site-specific expression of the opsin. For example, spatially targeted delivery of opsin-encoding gene is required in macula, which loses photosensitivity due to loss of photoreceptors in case of dry-AMD (97-99). With viral or other non-viral (e.g. electroporation, lipofection) method, the opsin constructs will be delivered everywhere, causing un-controlled expression over the whole retina. This will cause complications in functioning of non-degenerated areas of retina (100) by interference of light-evoked activities in multiple layers of the retinal circuitry. Therefore, application of spatially targeted NOD of opsins in degenerated retina will allow photo-stimulation of retinal cells in the areas of photoreceptor-degeneration, leading to vision restoration.

The invention provides a method of improving or restoring vision, comprising administering to a subject to the compositions described herein. Compositions of the mixture solution to be injected intravitreally or sub-retinal for vision restoration by the invented NOD method includes: (i) opsin plasmids, (ii) functionalized gold nano-rods and (iii) adjunctive for stabilization of molecules, or minimization of damage, or enhancement of their binding or mobility. For example, invention delivery is improvised by use of optimized formulation of Alpha-aminoadipic acid (AAA, a structural analogue of glutamate which is known to reversibly disturb the ILM (101, 102)) together with opsin-plasmid and GNRs to transiently permeabilize inner limiting membrane of human eye. Further, to allow promoter-specific expression of MCO in RGCs or bipolar cells, suitable promoter (i.e. γ-synuclein for RGC and mGluR6 for bipolar) is used upstream of opsin plasmid:

Surgical risks of existing complex retinal-implantation procedures for improving vision are very high. This is especially more of a concern in case of replacement of the implant due to device-failure during chronic usage. Further in diseases such as RP and dry-AMD, photodegeneration of retina advances at ~2 mm² per year. During such progressive loss, the NOD process can be easily repeated allowing opsin expression in new degenerated retinal area(s). Our proposed method of expression of opsin is easy-to-adapt into current clinical practice: (i) Intravitreal/sub-retinal injection and incubation of the functionalized gold nano-rods; (ii) Intravitreal/sub-retinal injection of opsin encoding plasmids; and (iii) Targeted NOD of opsin-plasmids into retinal cells in the photodegenerated areas based on imaging feedback.

NIR light beam (used for NOD) has practically negligible absorption coefficient in most of the tissues and transparent ocular layers such as the cornea, lens, and neural retina. Further, water absorption at near-infrared (~800-900 nm) nm (NOD laser beam) is minimal. However, the cw NIR light (used for NOD) may get absorbed by the retinal pigment epithelium. To minimize temperature rise (which may elicit damage to tissue), the NOD laser beam can be pulsated and the duty cycle is varied to achieve optimal effect (i.e. maximum delivery in retinal tissue without perturbing the retinal pigment epithelium).

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth above, are specifically incorporated by reference.

1. Luo D, Saltzman W M. Synthetic DNA delivery systems. Nat Biotech. 2000; 18(1):33-7.
2. Yu J-Y, DeRuiter S L, Turner D L. RNA interference by expression of short-interfering RNAs and hairpin RNAs in mammalian cells. Proc Nat Acad Sci. 2002; 99(9): 6047-52.
3. Burridge K, Feramisco J R. Microinjection and localization of a 130K protein in living fibroblasts: a relationship to actin and fibronectin. Cell. 1980; 19(3):587-95.
4. Akilov O E, Wu M X, Jin Y, Zhou Z, Geskin L J, Falo L D, et al. Vaccination with photodynamic therapy-treated macrophages induces highly suppressive T-regulatory cells. Photodermatol, Photoimmunol Photomed. 2011; 27(2):97-107.
5. Somia N, Verma I M. Gene therapy: trials and tribulations. Nat Rev Genet. 2000; 1(2):91-9.
6. Verma I M, Somia N. Gene therapy—promises, problems and prospects. Nature. 1997; 389(6648):239-42.
7. Tsien R Y. The Gree Fluorescent Protein. Ann Rev Biochem. 1998; 67(1):509-44.
8. Kamimura K, Suda T, Zhang G, Liu D. Advances in Gene Delivery Systems. Pharmaceut Med. 2011; 25(5):293-306.
9. Nagel G, Szellas T, Huhn W, Kateriya S, Adeishvili N, Berthold P, et al. Channelrhodopsin-2, a directly light-gated cation-selective membrane channel. Proc Nat Acad Sci. 2003; 100(24):13940-5.
10. Boyden E S, Zhang F, Bamberg E, Nagel G, Deisseroth K. Millisecond-timescale, genetically targeted optical control of neural activity. Nat Neurosci. 2005; 8(9):1263-8.
11. Han X, Boyden E S. Multiple-Color Optical Activation, Silencing, and Desynchronization of Neural Activity, with Single-Spike Temporal Resolution. PLoS ONE. 2007; 2(3):e299.
12. Zhang F, Aravanis A M, Adamantidis A, de Lecea L, Deisseroth K. Circuit-breakers: optical technologies for probing neural signals and systems. Nat Rev Neurosci. 2007; 8(8):577-81.
13. Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.
14. Method of the Year 2010. Nat Meth. 2011; 8(1):1-.
15. Deisseroth K. Optogenetics. Nat Meth. 2011; 8(1):26-9.
16. Fenno L, Yizhar O, Deisseroth K. The Development and Application of Optogenetics. Ann Rev Neurosci. 2011; 34(1):389-412.
17. Pastrana E. Optogenetics: controlling cell function with light. Nat Meth. 2011; 8(1):24-5.
18. Shivalingaiah S, Gu L, Mohanty S K. Non-linear stimulation of excitable cells with and without optogenetic sensitization. Proc SPIE 2011; 7883:788355.
19. Johansen J P, Hamanaka H, Monfils M H, Behnia R, Deisseroth K, Blair H T, et al. Optical activation of lateral amygdala pyramidal cells instructs associative fear learning. Proc Nat Acad Sci. 2010; 107(28):12692-7.
20. Tønnesen J, Parish C L, Sørensen A T, Andersson A, Lundberg C, Deisseroth K, et al. Functional Integration of Grafted Neural Stem Cell-Derived Dopaminergic Neurons Monitored by Optogenetics in an In Vitro Parkinson Model. PLoS ONE. 2011; 6(3):e17560.
21. Adamantidis A R, Tsai H C, Boutrel B, Zhang F, Stuber G D, Budygin E A, et al. Optogenetic interrogation of dopaminergic modulation of the multiple phases of reward-seeking behavior. J Neurosci. 2011; 31(30): 10829-35.
22. Alilain W J, Li X, Horn K P, Dhingra R, Dick T E, Herlitze S, et al. Light-Induced Rescue of Breathing after Spinal Cord Injury. J Neurosci. 2008; 28(46):11862-70.
23. Ivanova E, Roberts R, Bissig D, Pan Z-H, Berkowitz B A. Retinal channelrhodopsin-2-mediated activity in vivo evaluated with manganese-enhanced magnetic resonance imaging. J Molecular Vision. 2010; 16:1059-67.
24. Lagali P S, Balya D, Awatramani G B, Munch T A, Kim D S, Busskamp V, et al. Light-activated channels targeted to ON bipolar cells restore visual function in retinal degeneration. Nat Neurosci. 2008; 11(6):667-75.
25. Shivalingaiah S, Gu L, Mohanty S K. Correlation of spatial intensity distribution of light reaching the retina and restoration of vision by optogenetic stimulation. Proc SPIE. 2011; 7885:78851Y
26. Zufferey R, Nagy D, Mandel R J, Naldini L, Trono D. Multiply attenuated lentiviral vector achieves efficient gene delivery in vivo. Nat Biotech. 1997; 15(9):871-5.
27. Ruitenberg M J, Eggers R, Boer G J, Verhaagen J. Adeno-associated viral vectors as agents for gene delivery: application in disorders and trauma of the central nervous system. Methods. 2002; 28(2):182-94.
28. Naldini L, Blömer U, Gallay P, Ory D, Mulligan R, Gage F H, et al. In Vivo Gene Delivery and Stable Transduction of Nondividing Cells by a Lentiviral Vector. Science. 1996; 272(5259):263-7.
29. Thomas C E, Ehrhardt A, Kay M A. Progress and problems with the use of viral vectors for gene therapy. Nat Rev Genet. 2003; 4(5):346-58.
30. King R. Gene Delivery to Mammalian Cells by Microinjection. Methods in Molecular Biology. 2004; 245(2): 167-73.
31. Li S, Huang L. Nonviral gene therapy: promises and challenges. Gene Ther. 2000; 7(1):31-4.
32. Ferber D. Safer and Virus-Free? Science. 2001; 294 (5547):1638-42.
33. Newman C M, Lawrie A, Brisken A F, Cumberland D C. Ultrasound Gene Therapy: On the Road from Concept to Reality. Echocardiography. 2001; 18(4):339-47.
34. Templeton N S, Lasic D D, Frederik P M, Strey H H, Roberts D D, Pavlakis G N. Improved DNA: liposome complexes for increased systemic delivery and gene expression. Nat Biotech. 1997; 15(7):647-52.
35. Panyam J, Labhasetwar V. Biodegradable nanoparticles for drug and gene delivery to cells and tissue. Adv Drug Deliv Rev. 2003; 55(3):329-47.
36. Tao W, Wilkinson J, Stanbridge E J, Berns M W. Direct gene transfer into human cultured cells facilitated by laser micropuncture of the cell membrane. Proc Natl Acad Sci USA. 1987; 84(12):4180-4.
37. Schneckenburger H, Hendinger A, Sailer R, Strauss W S, Schmitt M. Laser-assisted optoporation of single cells. J Biomed Opt. 2002; 7(3):410-6.
38. Palumbo G, Caruso M, Crescenzi E, Tecce M F, *Roberti* G, Colasanti A. Targeted gene transfer in eucaryotic cells by dye-assisted laser optoporation. J Photochem Photobiol B. 1996; 36(1):41-6.
39. Mohanty S K, Sharma M, Gupta P K. Laser-assisted microinjection into targeted animal cells. Biotech Lett. 2003; 25(11):895-9.
40. Hosokawa Y, Iguchi S, Yasukuni R, Hiraki Y, Shukunami C, Masuhara H. Gene delivery process in a single animal cell after femtosecond laser microinjection. Appl Surf Sci. 2009; 255(24):9880-4.
41. Stracke F, Rieman I, König K. Optical nanoinjection of macromolecules into vital cells. Journal of Photochemistry and Photobiology B: Biology. 2005; 81(3):136-42.
42. Schinkel H, Jacobs P, Schillberg S, Wehner M. Infrared picosecond laser for perforation of single plant cells. Biotechnol Bioeng. 2008; 99(1):244-8.
43. Tirlapur U K, Konig K. Targeted transfection by femtosecond laser. Nature. 2002; 418(6895):290-1.
44. Tirlapur U K, Konig K. Femtosecond near-infrared laser pulses as a versatile non-invasive tool for intra-tissue nanoprocessing in plants without compromising viability. Plant J. 2002; 31(3):365-74.

45. Gu L, Mohanty S K. Targeted microinjection into cells and retina using optoporation. J Biomed Opt. 2011; 16(12):128003-6.
46. Dhakal K, Black B, Mohanty S. Introduction of impermeable actin-staining molecules to mammalian cells by optoporation. Sci Rep. 2014; 4(6553):1-7.
47. Grunwald J E, Pistilli M, Ying G S, Maguire M G, Daniel E, Martin D F. Growth of Geographic Atrophy in the Comparison of Age-related Macular Degeneration Treatments Trials. Ophthalmology. 2014.
48. Wu Z, Ayton L N, Luu C D, Guymer R H. Microperimetry of nascent geographic atrophy in age-related macular degeneration. Invest Ophthalmol Vis Sci. 2015; 56(1):115-21.
49. Wallsh J, Gallemore R. Optical coherence tomography difference maps and average macular volume for geographic atrophy. Retin Cases Brief Rep. 2015; 9(1):88-91.
50. Biarnes M, Mones J, Alonso J, Arias L. Update on geographic atrophy in age-related macular degeneration. Optom Vis Sci. 2011; 88(7):881-9.
51. Sunness J S, Margalit E, Srikumaran D, Applegate C A, Tian Y, Perry D, et al. The long-term natural history of geographic atrophy from age-related macular degeneration: enlargement of atrophy and implications for interventional clinical trials. Ophthalmology. 2007; 114(2):271-7.
52. Wang S, Chen K J, Wu T H, Wang H, Lin W Y, Ohashi M, et al. Photothermal Effects of Supramolecularly Assembled Gold Nanoparticles for the Targeted Treatment of Cancer Cells. Angewandte Chemie. 2010; 122(22):3865-9.
53. Cheng Y, Samia A C, Li J, Kenney M E, Resnick A, Burda C. Delivery and efficacy of a cancer drug as a function of the bond to the gold nanoparticle surface. Langmuir. 2010; 26(4):2248-55.
54. Kim B, Han G, Toley B J, Kim C-k, Rotello V M, Forbes N S. Tuning payload delivery in tumour cylindroids using gold nanoparticles. Nat Nano. 2010; 5(6):465-72.
55. Tong L, Zhao Y, Huff T, Hansen M, Wei A, Cheng J X. Gold Nanorods Mediate Tumor Cell Death by Compromising Membrane Integrity. Advanced Materials. 2007; 19(20):3136-41.
56. Huang X, El-Sayed I H, Qian W, El-Sayed M A. Cancer Cell Imaging and Photothermal Therapy in the Near-Infrared Region by Using Gold Nanorods. Journal of the American Chemical Society. 2006; 128(6):2115-20.
57. Gobin A M, Lee M H, Halas N J, James W D, Drezek R A, West J L. Near-Infrared Resonant Nanoshells for Combined Optical Imaging and Photothermal Cancer Therapy. Nano Letters. 2007; 7(7):1929-34.
58. Brongersma M L. Nanoscale photonics: Nanoshells: gifts in a gold wrapper. Nat Mater. 2003; 2(5):296-7.
59. Chen J, Wang D, Xi J, Au L, Siekkinen A, Warsen A, et al. Immuno Gold Nanocages with Tailored Optical Properties for Targeted Photothermal Destruction of Cancer Cells. Nano Letters. 2007; 7(5):1318-22.
60. Chen J, Saeki F, Wiley B J, Cang H, Cobb M J, Li Z-Y, et al. Gold Nanocages: Bioconjugation and Their Potential Use as Optical Imaging Contrast Agents. Nano Letters. 2005; 5(3):473-7.
61. Sugano E, Isago H, Wang Z, Murayama N, Tamai M, Tomita H. Immune responses to adeno-associated virus type 2 encoding channelrhodopsin-2 in a genetically blind rat model for gene therapy. Gene Ther. 2011; 18(3):266-74.
62. Baumgartner W A. Etiology, pathogenesis, and experimental treatment of retinitis pigmentosa. Medical Hypotheses. 2000; 54(5):814-24.
63. Sahaboglu A, Paquet-Durand O, Dietter J, Dengler K, Bernhard-Kurz S, Ekstrom P A, et al. Retinitis pigmentosa: rapid neurodegeneration is governed by slow cell death mechanisms. Cell Death Dis. 2013; 4:e488.
64. Hamel C. Retinitis pigmentosa. Orphanet J Rare Dis. 2006; 1:40.
65. Busskamp V, Picaud S, Sahel J A, Roska B. Optogenetic therapy for retinitis pigmentosa. Gene Ther. 2012; 19(2):169-75.
66. Miller G. Shining New Light on Neural Circuits. Science. 2006; 314(5806):1674-6.
67. Zhang F, Wang L P, Boyden E S, Deisseroth K. Channelrhodopsin-2 and optical control of excitable cells. Nat Methods. 2006; 3(10):785-92.
68. Zhang F, Aravanis A M, Adamantidis A, de Lecea L, Deisseroth K. Circuit-breakers: optical technologies for probing neural signals and systems. Nat Rev Neurosci. 2007; 8(8):577-81.
69. Nagel G, Brauner M, Liewald J F, Adeishvili N, Bamberg E, Gottschalk A. Light activation of channelrhodopsin-2 in excitable cells of *Caenorhabditis elegans* triggers rapid behavioral responses. Curr Biol. 2005; 15(24):2279-84.
70. Schroll C, Riemensperger T, Bucher D, Ehmer J, Voller T, Erbguth K, et al. Light-induced activation of distinct modulatory neurons triggers appetitive or aversive learning in *Drosophila* larvae. Current Biology. 2006; 16(17):1741-7.
71. Cao H, Gu L, Mohanty S K, Chiao J C. An Integrated mu LED Optrode for Optogenetic Stimulation and Electrical Recording. Ieee T Bio-Med Eng. 2013; 60(1):225-9.
72. Dhakal K, Gu L, Shivalingaiah S, Dennis T, Bobzean S, Perrotti L, et al. Non-scanning fiber-optic near-infrared beam led to two-photon optogenetic stimulation in vivo. Plos One. 2014; in press.
73. Bi A D, Cui J J, Ma Y P, Olshevskaya E, Pu M L, Dizhoor A M, et al. Ectopic expression of a microbial-type rhodopsin restores visual responses in mice with photoreceptor degeneration. Neuron. 2006; 50(1):23-33.
74. Thyagarajan S, van Wyk M, Lehmann K, Lowel S, Feng G, Wassle H. Visual Function in Mice with Photoreceptor Degeneration and Transgenic Expression of Channelrhodopsin 2 in Ganglion Cells. J Neurosci. 2010; 30(26):8745-58.
75. Bi A, Cui J, Ma Y P, Olshevskaya E, Pu M, Dizhoor A M, et al. Ectopic expression of a microbial-type rhodopsin restores visual responses in mice with photoreceptor degeneration. Neuron. 2006; 50(1):23-33.
76. Zhang Y, Ivanova E, Bi A, Pan Z-H. Ectopic Expression of Multiple Microbial Rhodopsins Restores O N and OFF Light Responses in Retinas with Photoreceptor Degeneration. J Neurosci. 2009; 29(29):9186-96.
77. Tomita H, Sugano E, Isago H, Hiroi T, Wang Z, Ohta E, et al. Channelrhodopsin-2 gene transduced into retinal ganglion cells restores functional vision in genetically blind rats. Experimental Eye Research. 2010; 90(3):429-36.
78. Tomita H, Sugano E, Fukazawa Y, Isago H, Sugiyama Y, Hiroi T, et al. Visual Properties of Transgenic Rats Harboring the Channelrhodopsin-2 Gene Regulated by the Thy-1.2 Promoter. PLoS One. 2009; 4(11).
79. Doroudchi M M, Greenberg K P, Liu J, Silka K A, Boyden E S, Lockridge J A, et al. Virally delivered Channelrhodopsin-2 Safely and Effectively Restores Visual Function in Multiple Mouse Models of Blindness. Mol Ther. 2011; 19(7):1220-9.

80. Koizumi A, Tanaka K F, Yamanaka A. The manipulation of neural and cellular activities by ectopic expression of melanopsin. Neurosci Res. 2013; 75(1):3-5.

81. Fehrentz T, Schonberger M, Trauner D. Optochemical genetics. Angew Chem Int Ed Engl. 2011; 50(51):12156-82.

82. Fernandez de Castro J P, Scott P A, Fransen J W, Demas J, DeMarco P J, Kaplan H J, et al. Cone photoreceptors develop normally in the absence of functional rod photoreceptors in a transgenic swine model of retinitis pigmentosa. Invest Ophthalmol Vis Sci. 2014; 55(4):2460-8.

83. Busskamp V, Duebel J, Balya D, Fradot M, Viney T J, Siegert S, et al. Genetic Reactivation of Cone Photoreceptors Restores Visual Responses in Retinitis Pigmentosa. Science. 2010; 329(5990):413-7.

84. Kraszewski K, Mundigl O, Daniell L, Verderio C, Matteoli M, De Camilli P. Synaptic vesicle dynamics in living cultured hippocampal neurons visualized with CY3-conjugated antibodies directed against the lumenal domain of synaptotagmin. J Neurosci. 1995; 15(6):4328-42.

85. Kavalali E T, Jorgensen E M. Visualizing presynaptic function. Nat Neurosci. 2014; 17(1):10-6.

86. Hartong D T, Berson E L, Dryja T P. Retinitis pigmentosa. Lancet. 2006; 368(9549):1795-809.

87. Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.

88. Daiger S P, Bowne S J, Sullivan L S. Perspective on genes and mutations causing retinitis pigmentosa. Arch Ophthalmol. 2007; 125(2):151-8.

89. Mezer E, Babul-Hirji R, Wise R, Chipman M, DaSilva L, Rowell M, et al. Attitudes Regarding Predictive Testing for Retinitis Pigmentosa. Ophthalmic Genetics. 2007; 28(1):9-15.

90. Flannery J G, Farber D B, Bird A C, Bok D. Degenerative changes in a retina affected with autosomal dominant retinitis pigmentosa. Invest Ophthalmol Vis Sci. 1989; 30(2):191-211.

91. Curcio C A, Medeiros N E, Millican C L. Photoreceptor loss in age-related macular degeneration. Invest Ophthalmol Vis Sci. 1996; 37(7):1236-49.

92. Hartong D T, Berson E L, Dryja T P. Retinitis pigmentosa. Lancet. 2006; 368(9549):1795-809.

93. Chader G J. Animal models in research on retinal degenerations: past progress and future hope. Vision Res. 2002; 42(4):393-9.

94. Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.

95. Grover S, Fishman G A, Anderson R J, Alexander K R, Derlacki D J. Rate of visual field loss in retinitis pigmentosa. Ophthalmology. 1997; 104(3):460-5.

96. Dichtl A, Jonas J B, Naumann G O. Retinal nerve fiber layer thickness in human eyes. Graefe's archive for clinical and experimental ophthalmology. 1999; 237(6):474-9.

97. Klein M L, Ferris F L, 3rd, Francis P J, Lindblad A S, Chew E Y, Hamon S C, et al. Progression of geographic atrophy and genotype in age-related macular degeneration. Ophthalmology. 2010; 117(8):1554-9, 9 e1.

98. Fleckenstein M, Schmitz-Valckenberg S, Adrion C, Kramer I, Eter N, Helb H M, et al. Tracking progression with spectral-domain optical coherence tomography in geographic atrophy caused by age-related macular degeneration. Invest Ophthalmol Vis Sci. 2010; 51(8):3846-52.

99. Sunness J S, Applegate C A, Bressler N M, Hawkins B S. Designing clinical trials for age-related geographic atrophy of the macula: enrollment data from the geographic atrophy natural history study. Retina. 2007; 27(2): 204-10.

100. Jacobson S G, Roman A J, Aleman T S, Sumaroka A, Herrera W, Windsor E A, et al. Normal central retinal function and structure preserved in retinitis pigmentosa. Invest Ophthalmol Vis Sci. 2010; 51(2):1079-85.

101. Pedersen O O, Karlsen R L. Destruction of Muller cells in the adult rat by intravitreal injection of D,L-alpha-aminoadipic acid. An electron microscopic study. Exp Eye Res. 1979; 28(5):569-75.

102. Ishikawa Y, Mine S. Aminoadipic Acid Toxic Effects on Retinal Glial-Cells. Jpn J Ophthalmol. 1983; 27(1):107-18.

What is claimed is:

1. A method of delivering a first agent to a first living cell type comprising:
   a. providing a first functionalized metal nanoparticle to a population of live cells, whereby said first nanoparticle binds a first living cell type;
   b. providing to said population of live cells a first agent;
   c. providing a first irradiation of said population of live cells with a continuous wave near-infrared laser beam tuned to a Surface Plasmon Resonance of said first functionalized metal nanoparticles, whereby said first living cell type bound by said first functionalized metal nanoparticles allow entry of said first agent into said first living cell type without entry of said first functionalized metal nanoparticles, and without killing the population of live cells.

2. The method according to claim 1, wherein following said first irradiation a second cell type is incapable of allowing entry of said first agent.

3. The method according to claim 1, wherein said first cell type is in said population of live cells and said method further comprises:
   a. providing a second functionalized metal nanoparticle to said population of live cells, whereby said second functionalized metal nanoparticle binds a living second cell type;
   b. providing to said population of live cells a second agent;
   c. providing a second irradiation of said population of live cells with a laser tuned to a Surface Plasmon Resonance of said second functionalized metal nanoparticle, whereby said second living cell type bound by said second functionalized metal nanoparticle allow entry of said second agent into said second living cell type without entry of said second functionalized metal nanoparticles, and without killing the population of live cells.

4. The method according to claim 3, wherein following said second irradiation the first living cell type is incapable of allowing entry of said second agent.

5. The method according to claim 1, wherein said first agent is a cell impermeable agent.

6. The method according to claim 5, wherein said cell impermeable agent is small molecules, nucleic acids or proteins.

7. The method according to claim 6, wherein said nucleic acids are siRNA, DNA, mRNA, modified siRNA, modified DNA or modified mRNA.

8. The method according to claim 7, wherein said DNA encodes a therapeutic protein.

9. The method according to claim 8, wherein said therapeutic protein is a cytokine, hormone, vaccine, opsin or antibody, or fragment thereof.

10. The method according to claim 9, wherein said first functionalized metal nanoparticle is gold nano-rods, said first agent is opsin plasmids, and said population of live cells is targeted retinal geographic atrophy areas for vision restoration in patients with retinal photodegeneration, wherein said method is used for optical delivery of opsin genes in targeted retinal geographic atrophy areas for vision restoration in patients with retinal photodegeneration by conventional intravitreal or sub-retinal injection of gold nano-rods and opsin plasmids, followed by said first irradiation of said targeted retinal geographic atrophy areas for vision restoration in patients with retinal photodegeneration with said continuous wave near-infrared laser beam tuned to the Surface Plasmon Resonance of said gold nano-rods.

11. The method according to claim 6, wherein said protein is a hormone, cytokine, antibody or fragment thereof.

12. The method according to claim 1, wherein said first population of live cells is in a tissue.

13. The method of claim 12, wherein the continuous wave near infrared laser beam is scanned over regions of interest of tissue requiring intra-cellular delivery of impermeable molecules.

14. The method of claim 12, wherein the continuous wave near infrared laser beam is pulsed, width varying from several picoseconds to minutes, in order to optimize delivery without overall heating of the population of live cells.

15. The method according to claim 12, wherein targeted molecular delivery by nano-enhanced optical delivery does not cause undesired expression in non-targeted cells and organs, or does not cause any adverse reaction or cytotoxicity in the targeted region.

16. The method of claim 12, wherein a reinjection and a transfection of said first functionalized metal nanoparticle and said first agent into said population of live cells is performed.

17. The method of claim 12, wherein said population of live cells are retina cells, and are ON-type ganglion cells or ON-type bipolar cells.

* * * * *

UNITED STATES PATENT AND TRADEMARK OFFICE
CERTIFICATE OF CORRECTION

PATENT NO. : 10,857,238 B2
APPLICATION NO. : 16/074041
DATED : December 8, 2020
INVENTOR(S) : Samarendra Kumar Mohanty et al.

Page 1 of 1

It is certified that error appears in the above-identified patent and that said Letters Patent is hereby corrected as shown below:

In the Claims

Column 30, Line 1, the word "first" should be deleted.

Signed and Sealed this
Nineteenth Day of January, 2021

Andrei Iancu
*Director of the United States Patent and Trademark Office*